United States Patent
Mrksich et al.

(10) Patent No.: US 11,047,861 B2
(45) Date of Patent: *Jun. 29, 2021

(54) CELLULAR ASSAYS WITH A MOLECULAR ENDPOINT MEASURED BY SAMDI MASS SPECTROMETRY

(71) Applicant: NORTHWESTERN UNIVERSITY, Evanston, IL (US)

(72) Inventors: Milan Mrksich, Hinsdale, IL (US); Eric J. Berns, Park Ridge, IL (US); Maria D. Cebezas, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 239 days.

This patent is subject to a terminal disclaimer.

(21) Appl. No.: 15/750,030

(22) PCT Filed: Aug. 8, 2016

(86) PCT No.: PCT/US2016/046027
§ 371 (c)(1),
(2) Date: Feb. 2, 2018

(87) PCT Pub. No.: WO2017/027468
PCT Pub. Date: Feb. 16, 2017

(65) Prior Publication Data
US 2018/0231564 A1 Aug. 16, 2018

Related U.S. Application Data

(60) Provisional application No. 62/202,417, filed on Aug. 7, 2015.

(51) Int. Cl.
*C12Q 1/37* (2006.01)
*C12Q 1/42* (2006.01)
(Continued)

(52) U.S. Cl.
CPC .......... *G01N 33/6851* (2013.01); *C12Q 1/00* (2013.01); *C12Q 1/26* (2013.01); *C12Q 1/37* (2013.01);
(Continued)

(58) Field of Classification Search
CPC ........ G01N 33/6851; C12Q 1/00; C12Q 1/26; C12Q 1/37; C12Q 1/42; C12Q 1/44; C12Q 1/46; C12Q 1/48; C12Q 1/485
See application file for complete search history.

(56) References Cited

U.S. PATENT DOCUMENTS 7,445,885 B2 * 11/2008 Heinzle .................. H01J 49/04
 205/209
9,046,527 B2 * 6/2015 Galisson ................ C07K 14/47
(Continued)

FOREIGN PATENT DOCUMENTS

WO WO-2016/138015 A1 9/2016
WO WO-2017/214151 A1 12/2017
(Continued)

OTHER PUBLICATIONS

Zhu, X.-Y. et al., Nov. 2001, American Chemical Society, Langmuir</i>, vol. 17, No. 25, 7798-7803 (Year: 2001).*
(Continued)

*Primary Examiner* — Jennifer Wecker
*Assistant Examiner* — Michael Paul Shimek
(74) *Attorney, Agent, or Firm* — Marshall, Gerstein & Borun LLP

(57) ABSTRACT

The disclosure provides a cell-based, label-free assay compatible with high-throughput screening (HTS) that can report quantitatively on enzyme activities by measuring mass changes of substrates with MALDI-mass spectrometry.

22 Claims, 10 Drawing Sheets

Specification includes a Sequence Listing.

(51) Int. Cl.

| | |
|---|---|
| *C12Q 1/00* | (2006.01) |
| *C12Q 1/44* | (2006.01) |
| *C12Q 1/48* | (2006.01) |
| *C12Q 1/26* | (2006.01) |
| *C12Q 1/46* | (2006.01) |
| *G01N 33/68* | (2006.01) |

(52) U.S. Cl.
CPC ................. *C12Q 1/42* (2013.01); *C12Q 1/44* (2013.01); *C12Q 1/46* (2013.01); *C12Q 1/48* (2013.01); *C12Q 1/485* (2013.01)

(56) References Cited

U.S. PATENT DOCUMENTS

| | | | |
|---|---|---|---|
| 2010/0011456 A1* | 1/2010 | Mathur | C12N 9/00 800/15 |
| 2010/0112722 A1 | 5/2010 | Mrksich et al. | |
| 2014/0134642 A1 | 5/2014 | Mrksich et al. | |
| 2015/0136972 A1* | 5/2015 | Lasch | G01N 33/569 250/282 |
| 2016/0252501 A1 | 9/2016 | Mrksich et al. | |
| 2018/0080058 A1 | 3/2018 | Mrksich et al. | |

FOREIGN PATENT DOCUMENTS

| | | |
|---|---|---|
| WO | WO-2019/168980 A1 | 9/2019 |
| WO | WO-2019/200262 A1 | 10/2019 |
| WO | WO-2019/237019 A1 | 12/2019 |

OTHER PUBLICATIONS

Min, Dal-Hee et al., Jul. 2004, American Chemical Society, Analytical Chemistry, vol. 76, No. 14, 3923-3929 (Year: 2004).*
Su, Jing et al., Apr. 2005, American Chemical Society, Journal of the American Chemical Society</i>, Iss. 127, 7280-7281 (Year: 2005).*
Su, Jing et al., Jul. 2006, American Chemical Society, Analytical Chemistry</i>, vol. 78, No. 14, 4945-4951 (Year: 2006).*
Bellis, Susan L., Jun. 2011, Biomaterials</i>, vol. 32, Iss. 18, 4205-4210 (Year: 2011).*
Arabaci et al., "α-Haloacetophenone Derovatoves as photoreversible Covalent Inhibotrs of Protein Tyrosine Phosphatases," J. Am. Chem. Soc. 121, (21), 5085-5086 (1999).
Ban et al., "Discovery of Glycosyltransferases Using Carbohydrate Arrays and Mass Spectrometry," Nat Chem Biol 8(9):769-773 (2012).
Ban et al., "On-Chip Synthesis and Label-Free Assays of Oligosaccharide Arrays," Angew Chem Int Ed Eng 47:3396-3399 (2008).
Bernard et al., "Staurosporine-induced apoptosis of HPV positive and negative human cervical cancer cells from different points in the cell cycle," Cell Death Differ 8: 234-244 (2001).
Cai et al., "Enzymatic Synthesis and Properties of Uridine-5'-O-(2-thiodiphospho)-N-acetylglucosamine," Carbohydr Res 346(12):1576-1580 (2011).
Deshmukh et al., "A regenerative approach to the treatment of multiple sclerosis," Nature, 502:327-332 (2013).
Dillmore et al., A photochemical method for patterning the immobilization of ligands and cells to self-assembled monolayers. *Langmuir*, 20: 7223-31 (2004).
Ding et al., "A role for chemistry in stem cell biology," Nat. Biotechnol, 22:833-840 (2004).
Feng et al., "The Synergy Peptide PHSRN and the Adhesion Peptide RGD Mediate Cell Adhesion through a Common Mechanism," Biochemistry 43:15811-15821 (2004).
Fox et al., "High-throughput screening: update on practices and success," J. Biomol. Screen., 11:864-869 (2006).
Gawalt et al., "A Substituent Effects Study Reveals the Kinetic Pathway for an Interfacial Reaction," J Am Chem Soc 126:15613-7 (2004).

Giepmans et al., "The fluorescent toolbox for assessing protein location and function," Science, 312:217-224 (2006).
Gurard-Levin et al., "Combining Mass Spectrometry and Peptide Arrays to Profile the Specificities of Histone Deacetylases," Chembiochem 10:2159-2161 (2009).
Gurard-Levin et al., "Combining Self-Assembled Monolayers and Mass Spectrometry for Applications in Biochips," Annu Rev Anal Chem 1:767-800 (2008).
Gurard-Levin et al., "High-Throughput Screening of Small Molecule Libraries using SAMDI Mass Spectrometry," ACS Comb Sci 13:347-350 (2011).
Gurard-Levin et al., "Peptide Arrays Identify Isoform-Selective Substrates for Profiling Endogenous Lysine Deacetylase Activity," ACS Chem Biol 5(9):863-873 (2010).
Gurard-Levin et al., "The Activity of HDAC8 Depends on Local and Distal Sequences of Its Peptide Substrates," Biochemistry 47:6242-6250 (2008).
Hellmuth et al., "Specific inhibitors of the protein tyrosine phosphatase Shp2 identified by high-throughput docking," Proc Natl Acad Sci U S A 105:7275-7280 (2008).
Hodneland et al., "Design of Self-Assembled Monolayers That Release Attached Groups Using Applied Electrical Potentials," Langmuir 13: 6001-6003 (1997).
Hodneland et al., "Selective immobilization of proteins to self-assembled monolayers presenting active site-directed capture ligands," Proc Natl Acad Sci USA 99: 5048-5052 (2002).
Hooff et al., "Characterization of Beta-Lactamase Enzyme Activity in Bacterial Lysates using MALDI-Mass Spectrometry," J. Proteome Res., 11:79-84 (2012).
Houseman et al., "Carbohydrate Arrays for the Evaluation of Protein Binding and Enzymatic Modification," Chem Biol 9: 443-454 (2002).
Houseman et al., "Environment of Arg-Gly-Asp ligands influences the adhesion of fibroblasts to self-assembled monolayers," Cell Attachment to the Extracellular Matrix, p. 430a, Abstract 2494 (1998).
Houseman et al., "Maleimide-Functionalized Self-Assembled Monolayers for the Preparation of Peptide and Carbohydrate Biochips," Langmuir 19: 1522-1531 (2003).
Houseman et al., "Model substrates for the dynamic control of cell behavior," Extracellular Matrix Cell Behavior, p. 45a, Abstract 232 (2000).
Houseman et al., "Model Systems for Studying Polyvalent Carbohydrate Binding Interactions," Top Curr Chem 218 1-44 (2002).
Houseman et al., "Peptide chips for the quantitative evaluation of protein kinase activity," Nat Biotechnol 20: 270-274 (2002).
Houseman et al., "The microenvironment of immobilized Arg-Gly-Asp peptides is an important determinant of cell adhesion," Biomaterials 22: 943-955 (2001).
Houseman et al., "The Role of Ligand Density in the Enzymatic Glycoslyation of Carbohydrates Presented on Self-Assembled Monolayers of Alkanethiolates on Gold," Angew Chem Int Ed 38: 782-785 (1999).
Houseman et al., "Towards quantitative assays with peptide chips: a surface engineering approach," Trends Biotechnol 20: 279-281 (2002).
Houseman et al., Using self-assembled monolayers that present Arg-Gly-Asp peptide ligands to study adhesion of fibroblasts. *Extracellular Matrix-Cell Interaction*, 11: p. A1095, Abstract 1395 (1997).
Inglese et al., "High-throughput screening assays for the identification of chemical probes," Nat. Chem. Biol. 3(8):466-479 (2007).
International Preliminary Report on Patentability for Application No. PCT/US2016/046027, dated Feb. 13, 2018.
International Search Report and Written Opinion for Application No. PCT/US2016/046027, dated Oct. 31, 2016.
James et al., Subcellular curvature at the perimeter of micropatterned cells influences lamellipodial distribution and cell polarity. *Cell Motil. Cytoskeleton*. 65: 841-52 (2008).
Johnson et al., "A stem cell-based approach to cartilage repair," Science, 336:717-721 (2012).
Kato et al., "Rewiring Cell Adhesion," J Am Chem Soc 126: 6504-6505 (2004).

(56) References Cited

OTHER PUBLICATIONS

Kato et al., "Using model substrates to study the influence of affinity on cell adhesion," Abstracts, Division of Biological Chemistry, 222nd National Meeting of the American Chemical Society, Aug. 26-29, 2001, Biochemistry 40: 8608-8608 (2001).
Kilian et al., "Directing stem cell fate by controlling the affinity and density of ligand-receptor interactions at the biomaterials interface," Angew Chem Int Ed Engl. 51(20):4891-5 (2012).
Kim et al., "Profiling the selectivity of DNA ligases in an array format with mass spectrometry," Nucleic Acids Res 38(1):e2, 10 pages (2010).
Kuo et al., Profiling Deacetylase Activities in Cell Lysates with Peptide Arrays and SAMDI Mass Spectrometry, Anal Chem 85:10635-10642 (2013).
Kwon et al., "Dependence of the Rate of an Interfacial Diels—Alder Reaction on the Steric Environment of the Immobilized Dienophile: An Example of Enthalpy-Entropy Compensation," J Am Chem Soc 124: 806-812 (2002).
Lang et al., "Cellular imaging in drug discovery," Nat. Rev. Drug Discov., 5:343-356 (2006).
Lee et al., "Protein Nanoarrays Generated by Dip-Pen Nanolithography," Science 295:1702-1705 (2002).
Li et al., "Catalytic Asymmetric Dihydroxylation by Gold Colloids Functionalized with Self-Assembled Monolayers," Langmuir 15: 4957-4959 (1999).
Li et al., "Rapid Evaluation and Screening of Interfacial Reactions on Self-Assembled Monolayers," Langmuir 23:11826-11835 (2007).
Li et al., "Steady-State of an Enzymatic Reaction is Dependent on the Density of Reactant," Langmuir 29:294-298 (2013).
Liao et al., "A Spatially Propagating Biochemical Reaction," Angew Chem Int Ed Engl 50:706-708 (2011).
Liao et al., "An Adaptor Domain-Mediated Auto-Catalytic Interfacial Kinase Reaction," Chemistry 15(14):12303-12309 (2009).
Luk et al., "Self-Assembled Monolayers of Alkanethiolates Presenting Mannitol Groups Are Inert to Protein Adsorption and Cell Attachment," Langmuir 16: 9604-9608 (2000).
Luk et al., "Sterochemical Control of Cell Adhesion on Self-Assembled Monolayers Presenting Organized Saccharides: Potential Effect of Templated Water Structure," Biochemistry 42: 8647-8647 (2003).
Macarron et al., "Impact of high-throughput screening in biomedical research," Nat. Rev. Drug Discov., 10:188-195 (2011).
Marin et al., "Functional Assays of Membrane-Bound Proteins with SAMDI-TOF Mass Spectrometry," Angew Chem Int Ed Engl 46(46):8796-8798 (2007).
Min et al., "A Method for Connecting Solution-Phase Enzyme Activity Assays with Immobilized Format Analysis by Mass Spectrometry," Anal Chem 76:3923-3929 (2004).
Min et al., "Chemical screening by mass spectrometry to identify inhibitors of anthrax lethal factor," Nat. Biotechnol., 22:717-723 (2004).
Min et al., "Peptide arrays: towards routine implementation," Curr Opin Chem Biol 8:554-558 (2004).
Min et al., "Profiling Kinase Activities by Using a Peptide Chip and Mass Spectrometry," Angewandte Chemie 43:5973-5977 (2004).
Montavon et al., "Three-Component Reaction Discovery Enabled by Mass Spectrometry of Self-Assembled Monolayers," Nat Chem 4(1):45-51 (2012).
Moore et al., "The Development of β-Lactamase as a Highly Versatile Genetic Reporter for Eukaryotic Cells," Anal. Biochem., 247:203-209 (1997).
Mrksich et al., "Using Self-Assembled Monolayers that Present Oligo(ethylene glycol) Groups to Control the Interactions of Proteins with Surfaces," Acs Sym Ser 680: 361-373 (1997).
Mrksich et al., "Using Self-Assembled Monolayers to Understand the Interactions of Man-Made Surfaces with Proteins and Cells," Annu Rev Biophys Biomol Struct 25: 55-78 (1996).
Mrksich, "A surface chemistry approach to studying cell adhesion," Chem Soc Rev 29: 267-273 (2000).
Mrksich, "Dynamic Substrates for Cell Biology," MRS Bull 30:180-184 (2005).
Mrksich, "Mass Spectrometry of Self-Assembled Monolayers: A New Tool for Molecular Surface Science," ACS Nano 2(1):7-18 (2008).
Mrksich, "Tailored substrates for studies of attached cell culture," Cell Mol Life Sci 54: 653-662 (1998).
Mrksich, "Using self-assembled monolayers to understand the biomaterials interface," Curr Opin Colloid In 2: 83-88 (1997).
Mrksich, "What can surface chemistry do for cell biology?", Curr Opin Chem Biol 6: 794-797 (2002).
Murphy et al., "Substrates for Cell Adhesion Prepared Via Active Site-Directed Immobilization of a Protein Domain," Langmuir 20:1026-1030 (2004).
O'Rourke et al., "Protein localization studies in the age of 'Omics," Curr. Opin. Chem. Biol., 9(1):82-87 (2005).
Patel et al., "Discovery of SIRT3 Inhibitors Using SAMDI Mass Spectrometry," J. Biomol. Screen 20(7):842-848 (2015).
Patrie et al., "Self-Assembled Monolayers for MALDI-TOF Mass Spectrometry for Immunoassays of Human Protein Antigens," Anal Chem 79:5878-5887 (2007).
Perlman et al., "Multidimensional drug profiling by automated microscop," Science, 306:1194-1198 (2004).
Prats-Alfonso et al., "Cancer Prognostics by Direct Detection of p53-Antibodies on Gold Surfaces by Impedance Measurements," Small 8(13):2106-2115 (2012).
Roberts et al., "Using Mixed Self-Assembled Monolayers Presenting RGD and (EG)3OH Groups to Characterize Long-Term Attachment of Bovine Capillary Endothelial Cells to Surfaces," Journal of the American Chemical Society 120:6548-6555 (1998).
Ruoslahti et al., "RGD and Other Recognition Sequences for Integrins," Annu. Rev. Cell Dev. Biol. 12:697-715 (1996).
Su et al., "Assays of Endogenous Caspase Activities: A Comparison of Mass Spectrometry and Fluorescence Formats," Anal. Chem., 78:4945-4951 (2006).
Su et al., "Using MALDI-TOF Mass Spectrometry to Characterize Interfacial Reactions on Self-Assembled Monolayers," Langmuir 19(12):4867-4870 (2003).
Su et al., "Using Mass Spectrometry to Characterize Self-Assembled Monolayers Presenting Peptides, Proteins, and Carbohydrates," Angew Chem Int Ed Eng. 41(24):4715-4718 (2002).
Ting et al., "Genetically encoded fluorescent reporters of protein tyrosine kinase activities in living cells," Proc Natl Acad Sci U S A 98:15003-15008 (2001).
Tsien et al., "The Green Fluorescent Protein," Annu. Rev. Biochem. 67:509-544 (1998).
Tsubery et al., "Biochemical Assays of Immobilized Oligonucleotides with Mass Spectrometry," Langmuir 24:5433-5438 (2008).
Wehrman et al., "Enzymatic detection of protein translocation," Nat. Methods, 2(7):521-527 (2005).
Whitney et al., "A Genome-Wide Functional Assay of Signal Transduction in Living Mammalian Cells," Nat. Biotechnol., 16:1329-1333 (1998).
Yeo et al., "Electroactive Monolayer Substrates that Selectively Release Adherent Cells," Chembiochem 2: 590-593 (2001).
Yeo et al., "Electroactive Substrates that Reveal Aldehyde Groups for Bio-Immobilization," Adv Mater 16(15):1352-1356 (2004).
Yeo et al., "Label-Free Detection of Protein-Protein Interactions on Biochips," Angew Chem Int Ed Engl 44:5480-5483 (2005).
Yeo et al., "Self-Assembled Monolayers That Transduce Enzymatic Activities to Electrical Signals," Angew Chem Int Ed Engl 42: 3121-3124 (2003).
Yonzon et al., "A Comparative Analysis of Localized and Propagating Surface Plasmon Resonance Sensors: The Binding of Concanavalin A to a Monosaccharide Functionalized Self-Assembled Monolayer," J Am Chem Soc 126:12669-12676 (2004).
Yousaf et al., "Diels-Alder Reaction for the Selective Immobilization of Protein to Electroactive Self-Assembled Monolayers," J Am Chem Soc 121: 4286-4287 (1999).
Yousaf et al., "Electroactive substrates that modulate cell growth," Abstract 170, p. 1580, Biochemistry 39(6):1542-1582 (2000).

(56) References Cited

OTHER PUBLICATIONS

Yousaf et al., "The Kinetic Order of an Interfacial Diels-Alder Reaction Depends on the Environment of the Immobilized Dienophile," Angew Chem Int Ed Engl 39: 1943-1946 (2000).
Yousaf et al., "Turning on Cell Migration with Electroactive Substrates," Angew Chem Int Ed Engl 40: 1093-1096 (2001).
Yousaf et al., "Using electroactive substrates to pattern the attachment of two different cell populations," Proc Natl Acad Sci USA 98: 5992-5996 (2001).
Zhang et al., "A Simple Statistical Parameter for Use in Evaluation and Validation of High Throughput Screening Assays," J Biomol Screen 4:67-73 (1999).
Zhang et al., "Genetically encoded reporters of protein kinase A activity reveal impact of substrate tethering," Proc Natl Acad Sci U S A 98:14997-15002 (2001).
Zlokarnik et al., "Quantitation of transcription and clonal selection of single living cells with beta-lactamase as reporter," Science, 279:84-88 (1998).
Berns et al., "Cellular Assays with a Molecular Endpoint Measured by SAMDI Mass Spectrometry," Small 12(28):3811-3818 (2016).
Kato et al., "Using Model Substrates to Study the Dependence of Focal Adhesion Formation on the Affinity of Integrin-Ligand Complexes," Biochemistry 43:2699-2707 (2004).

\* cited by examiner

CELLULAR ASSAYS WITH A MOLECULAR ENDPOINT MEASURED BY SAMDI MASS SPECTROMETRY

CROSS REFERENCE TO RELATED APPLICATIONS

This application is a U.S. National Phase of International Application No. PCT/US2016/46027 filed Aug. 8, 2016, which claims the benefit of U.S. Provisional Application Ser. No. 62/202,417, filed Aug. 7, 2015, the disclosures of which are incorporated herein by reference in their entirety.

STATEMENT OF GOVERNMENT INTEREST

This invention was made with government support under U54 CA199091 awarded by the National Institutes of Health. The government has certain rights in the invention.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 2015-129_Seqlisting.txt; Size: 1,022 bytes, created: Aug. 8, 2016.

FIELD OF THE INVENTION

The present disclosure is directed to high throughput, label-free methods of profiling enzyme-substrate interactions.

BACKGROUND OF THE INVENTION

Cell-based assays are finding increasing use in modern drug discovery screens because they enable the concomitant evaluation of compound permeability, toxicity and activity within a more physiologically relevant cellular environment [Fox et al., J. Biomol. Screen. 2006, 11; Macarron et al., Nat. Rev. Drug Discov. 2011, 10]. However, cell-based assays that measure the activities of specific enzymes can be substantially more difficult to implement than biochemical assays. The common strategies for measuring enzyme activities—including those based on absorbance, fluorescence and radioactivity—often require reagents that cannot be delivered to the appropriate cellular compartment or are not compatible with the cellular environment.

Most cell-based screens use gene expression or phenotypic changes as a readout and require a labeled reporter in addition to compatibility with automated data acquisition and analysis methods. Gene expression reporter systems, such as β-lactamase paired with fluorescence resonance energy transfer (FRET) [Zlokarnik et al., Science 1998, 279], fluorogenic [Whitney et al., Nat. Biotechnol. 1998, 16], or chromogenic [Moore et al., Anal. Biochem. 1997, 247] substrates, have been of significant value in cell-based screening [Inglese et al., Nat. Chem. Biol. 2007, 3]. Protein and other biomolecule labeling methods, including genetic encoding of fusion proteins incorporating fluorescent proteins [Tsien, Annu. Rev. Biochem. 1998, 67], chromophoric, fluorescent, and immuno-labeling [Giepmans et al., Science 2006, 312], have been used to visualize protein expression [Deshmukh et al., Nature 2013, 502], localization [O'Rourke et al., Curr. Opin. Chem. Biol. 2005, 9], and translocation between cellular compartments [Wehrman et al., Nat. Methods 2005, 2]. High content screens (with automated image acquisition and analysis) using these methods have been used to identify compounds that produce desired molecular and phenotypic changes [Ding, P. G. Schultz, Nat. Biotechnol. 2004, 22; Johnson et al., Science 2012, 336; Perlman et al., Science 2004, 306; Lang et al., Nat. Rev. Drug Discov. 2006, 5].

Previous work has developed SAMDI mass spectrometry as a label-free assay for measuring enzyme activities [Min et al., Anal. Chem. 2004, 76; Ban et al., Nat. Chem. Biol. 2012, 8; Gurard-Levin et al., Anal. Chem. 2013, 85; Min et al., Angew. Chem. Int. Ed. Engl. 2004, 43; Mrksich, ACS Nano 2008, 2; Su et al., Anal. Chem. 2006, 78; Min et al., Nat. Biotechnol. 2004, 22]. In SAMDI, an enzyme substrate is immobilized to a self-assembled monolayer presenting tri(ethylene glycol) groups. The substrate can be immobilized through a variety of chemical reactions and the glycol groups serve the important role of preventing non-specific adsorption of proteins to the surface, giving a more quantitative measure of activity. Further, these monolayers are well-suited for analysis by matrix-assisted laser desorption/ionization mass spectrometry (MALDI-MS) because irradiation of the monolayer with a laser results in dissociation of the thiolate-gold bond and release of the intact alkanethiolates. In this way, treatment of the immobilized peptide with an enzyme that can modify its structure will result in a change in mass of the peptide-alkanethiolate conjugate, which can be directly observed in the SAMDI spectrum.

SUMMARY OF THE INVENTION

High-throughput screening (HTS) is a key tool used in the discovery of new molecular entities. Assays performed in which screened compounds are applied to cells are increasingly used in drug discovery, but currently used technologies frequently rely on readouts of gene expression or phenotypic changes. These assays often require development of specialized labeled reporters for each new target. The present disclosure provides a cell-based, label-free assay compatible with HTS that reports quantitatively on enzyme activities. The assay uses self-assembled monolayers to culture cells on arrays as well as to present substrates, which serve as reporters for a desired enzyme activity. Treatment of each spot on the array with compounds, followed by the generation of independent lysates enables the assay to be applied to screens.

In general, the technology combines cell lysis with a label-free assay of enzyme activities in the lysate. The assay uses SAMDI, where the monolayers are engineered to present enzyme substrates together with a peptide that supports cell adhesion on the assay chip. In this way, lysis of a population of cells occurs in the presence of peptide substrates, where enzymes in the lysate can directly and immediately act on the immobilized substrates. The monolayer is then rinsed and analyzed by SAMDI mass spectrometry to quantitate the amount of product (FIG. 1). This approach, termed Tandem Culture and Lysis-SAMDI (TCAL-SAMDI) provides a general method for conducting cell-based, chemical screening with quantitative readouts of enzymatic activity, easily adaptable to a wide range of targets.

Accordingly, in some aspects the disclosure provides a method of assaying activity of an intracellular enzyme, comprising (a) contacting a cell and a surface, the surface comprising an immobilized cell adhesion ligand and an immobilized substrate for the enzyme, the contacting resulting in immobilization of the cell via interaction between the cell and the immobilized cell adhesion ligand; (b) contacting the cell with a lysing solution to form a cell lysate and release the enzyme, thereby allowing contact between the enzyme and the immobilized substrate to transform the immobilized substrate to a product, the product having a different mass than the substrate; and (c) measuring the amount of the product formed using matrix-assisted laser desorption/ionization mass spectrometry (MALDI-MS) to assay the activity of the enzyme. In some embodiments, the surface comprises a multi-well plate. In further embodiments, the surface comprises gold, silver, or copper.

The disclosure also provides embodiments wherein more than one cell is applied to the monolayer. In related embodiments, 2, 5, 10, 20, 50, or 100 cells are applied to the monolayer.

In some embodiments, at least one of the immobilized substrate and the cell adhesion ligand comprises a peptide. In further embodiments, the peptide is bound to the surface via a cysteine residue. In some embodiments, the cell adhesion ligand comprises a RGD peptide.

In further embodiments, at least one of the cell adhesion ligand and the immobilized substrate is bound to the surface via a linker. The linker, in various embodiments, has a structure of formula I:

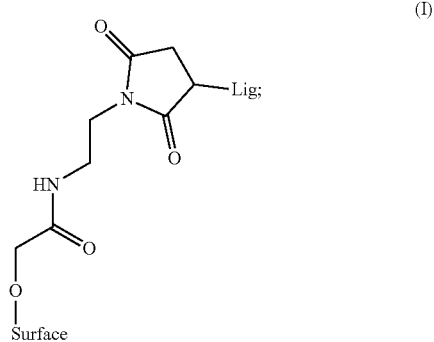

and Lig comprises the cell adhesion ligand or the immobilized substrate.

In some embodiments, the surface comprises a monolayer. In further embodiments, the monolayer comprises (i) the linker and (ii) an ethylene glycol and a $C_{2-20}$alkylene moiety. In still further embodiments, the monolayer is attached to the surface via a thiol bond.

In various embodiments, the enzyme is a deacetylase, acetyltransferase, esterase, phosphorylase/kinase, phosphatase, protease, methylase, demethylase, or a DNA or RNA modifying enzyme. In some embodiments, the deacetylase is KDAC8. In further embodiments, the esterase is cutinase or acetylcholine esterase. In additional embodiments, the protease is TEV. In some embodiments, the enzyme a caspase. In still further embodiments, the phosphatase is an acid phosphatase, alkaline phosphatase, protein tyrosine phosphatase or serine/threonine phosphatase.

In some embodiments, the immobilized substrate comprises an acylated peptide and the product comprises a deacylated peptide. In further embodiments, the immobilized substrate comprises a deacylated peptide and the product comprises an acylated peptide.

In further embodiments, the immobilized substrate comprises a phosphorylated peptide and the product comprises a dephosphorylated peptide. In yet additional embodiments, the immobilized substrate comprises a dephosphorylated peptide and the product comprises a phosphorylated peptide.

In some embodiments, the immobilized substrate comprises a methylated peptide and the product comprises a demethylated peptide. In further embodiments, the immobilized substrate comprises a demethylated peptide and the product comprises a methylated peptide.

In any of the embodiments disclosed herein, the disclosure provides methods further comprising washing the surface after immobilizing the cell on the surface and before lysing the cell to remove all cells not immobilized onto the surface.

In some embodiments, the surface comprises a second immobilized substrate that associates with a second enzyme in the cell lysate to form a second product, the second product having a different mass than the second substrate.

In any of the embodiments of the disclosure, the lysate comprises a potential modulator of binding of the enzyme and the immobilized substrate; and the activity of the enzyme assayed indicates the potential modulator's effect on the binding of the enzyme and the immobilized substrate in the presence of the potential modulator. In some embodiments, the lysate comprises a second potential modulator of binding of the second enzyme and the second immobilized substrate; and the activity of the second enzyme assayed indicates the second potential modulator's effect on the binding of the second enzyme and the second immobilized substrate in the presence of the second potential modulator. In further embodiments, the potential modulator or the second potential modulator is an inhibitor of the enzyme and immobilized substrate binding. In still further embodiments, the potential modulator or the second potential modulator is an activator of the enzyme and immobilized substrate binding.

DETAILED DESCRIPTION

Figure 1:
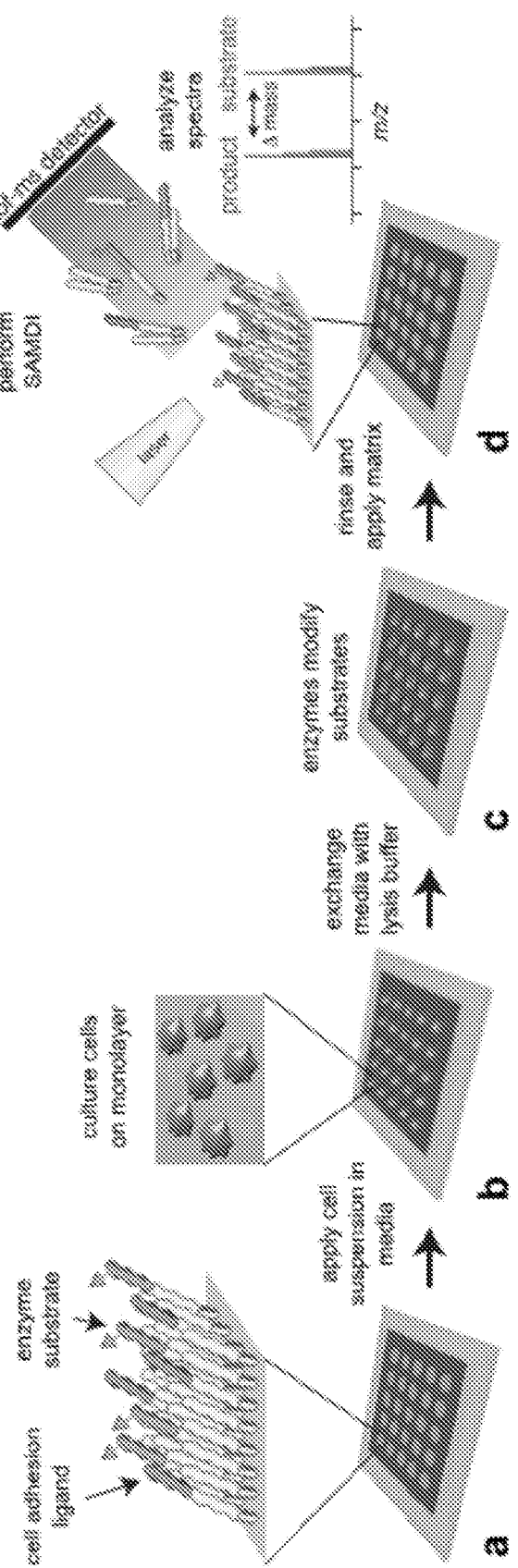
FIG. 1 depicts Tandem Culture and Lysis-SAMDI (TCAL-SAMDI). (a) Monolayers presenting both a cell adhesion ligand and an enzyme substrate are prepared on arrays of gold spots. (b) Cells are cultured on the monolayers and independently treated. (c) Media is replaced with lysis buffer, releasing enzymes from cells that can then modify the immobilized substrates. (d) The surfaces are rinsed, coated with matrix, and measured by SAMDI-mass spectrometry, revealing the extent of conversion of substrate to product.

The present disclosure describes methods for measuring enzyme activities, such as enzyme activities measured from a cell lysate. The methods are based on the SAMDI mass spectrometry technique (U.S. Patent Application Publication Number 2010/0112722, incorporated herein by reference in its entirety) and use matrix-assisted laser desorption-ionization mass spectrometry to analyze self-assembled monolayers.

Self-Assembled Monolayer Substrates.

The present disclosure contemplates the use of self-assembled monolayers as substrates for assay applications (Mrksich et al., Annu Rev Biophys Biomol Struct 25: 55-78 (1996); Hodneland et al., Langmuir 13: 6001-6003 (1997); Houseman et al., FASEB J 11: A1095-A1095 (1997); Mrksich, Curr Opin Colloid In 2: 83-88 (1997); Mrksich et al., Acs Sym Ser 680: 361-373 (1997); Houseman et al., Mol Biol Cell 9: 430a-430a (1998); Mrksich, Cell Mol Life Sci 54: 653-662 (1998); Houseman et al., Angew Chem Int Ed 38: 782-785 (1999); Li et al., Langmuir 15: 4957-4959 (1999); Yousaf et al., J Am Chem Soc 121: 4286-4287 (1999); Houseman et al., Mol Biol Cell 11: 45a-45a (2000); Luk et al., Langmuir 16: 9604-9608. (2000); Mrksich, Chem Soc Rev 29: 267-273 (2000); Yousaf et al., Angew Chem Int Ed Engl 39: 1943-1946 (2000); Yousaf et al., Biochemistry 39: 1580-1580 (2000); Houseman et al., Biomaterials 22: 943-955 (2001); Kato et al., Biochemistry 40: 8608-8608 (2001); Yeo et al., Chembiochem 2: 590-593 (2001); Yousaf et al., Proc Natl Acad Sci USA 98: 5992-5996. (2001); Yousaf et al., Angew Chem Int Ed Engl 40: 1093-1096 (2001); Hodneland et al., Proc Natl Acad Sci USA 99: 5048-5052 (2002); Houseman et al., Nat Biotechnol 20: 270-274 (2002); Houseman et al., Top Curr Chem 218: 1-44 (2002); Houseman et al., Trends Biotechnol 20: 279-281 (2002); Houseman et al., Chem Biol 9: 443-454 (2002); Kwon et al., J Am Chem Soc 124: 806-812 (2002); Lee et al., Science 295: 1702-1705 (2002); Mrksich, Curr Opin Chem Biol 6: 794-797 (2002); Houseman et al., Langmuir 19: 1522-1531 (2003); Luk et al., Biochemistry 42: 8647-8647 (2003); Yeo et al., Angew Chem Int Ed Engl 42: 3121-3124 (2003); Dillmore et al., Langmuir 20: 7223-7231 (2004); Feng et al., Biochemistry 43: 15811-15821 (2004); Kato et al., J Am Chem Soc 126: 6504-6505 (2004); Min et al., Curr Opin Chem Biol 8: 554-558 (2004); Murphy et al., Langmuir 20: 1026-1030 (2004); Yeo et al., Adv Mater 16: 1352-1356 (2004); Yonzon et al., J Am Chem Soc 126: 12669-12676 (2004); Mrksich, MRS Bull 30: 180-184 (2005); James et al., Cell Motil Cytoskeleton 65: 841-852 (2008)). Previous work utilized a monolayer that presented a peptide against a background of tri(ethylene glycol) groups (Houseman et al., Nat Biotechnol 20: 270-274 (2002)). The peptide was a substrate for Src kinase and the glycol groups prevented non-specific adsorption of protein to the monolayer. Treatment of the monolayer with enzyme and ATP resulted in phosphorylation of the peptide, which was detected by measuring radioactivity from a $^{32}P$ label or by using an anti-phosphotyrosine antibody with detection by fluorescence scanning or surface plasmon resonance spectroscopy. This example showed that the use of monolayers gave solid-phase assay with exceptional performance. It further indicated that blocking procedures were unnecessary; the signal was 80-fold above background; and that enzyme constants and inhibitor dissociation constants could be measured quantitatively. The monolayers offer the benefits that immobilized ligands are presented in a homogeneous environment and the density of the immobilized ligands can be controlled and made uniform across the entire array (Gawalt et al., J Am Chem Soc 126: 15613-7 (2004)). The monolayers are also compatible with a range of immobilization chemistries (Montavon et al., Nat Chem 4: 45-51 (2012); Ban et al., Nat Chem Biol 8: 769-773 (2012); Li et al., Langmuir 23, 11826-11835 (2007)). In these respects, the monolayers are more effective as substrates in assay applications than is the nitrocellulose material, or even the common use of glass. A significant additional benefit of the monolayer substrates is that they can be analyzed by matrix-assisted laser desorption-ionization mass spectrometry (i.e., SAMDI mass spectrometry) and therefore provide a route to label-free assays of biochemical activities (Su et al., Langmuir 19: 4867-4870 (2003)).

SAMDI Mass Spectrometry

SAMDI mass spectrometry can be used to detect the mass of a substrate or product. In this way, when the monolayer is treated with an enzyme that modifies the immobilized substrate, the resulting mass change of the immobilized product can be detected with mass spectrometry. The assay is applicable to a broad range of post-translational activities, can be performed in high throughput using plates having a number of distinct reaction zones (e.g., 1536 or 384) offering a throughput of about 50,000 assays per day, and is quantitative with Z-factors greater than 0.8. The assay can also be used to screen small molecule libraries to identify inhibitors or activators of enzymes.

In SAMDI, the monolayer is irradiated with a laser, which results in desorption of the products and substrates through dissociation of a thiolate-gold bond, but with little fragmentation of these molecules. Hence, the resulting spectra are straightforward to interpret. Assays using this SAMDI technique can be used on a range of enzyme activities, and are quantitative, compatible with complex lysates, and adaptable to high throughput formats (Ban et al., Nat Chem Biol 8: 769-773 (2012); Li et al., Langmuir 23: 11826-11835 (2007); Su et al., Langmuir 19: 4867-4870 (2003); Su et al., Angew Chem Int Ed Eng. 41: 4715-4718 (2002); Min et al., Angewandte Chemie 43: 5973-5977 (2004); Min et al., Anal Chem 76: 3923-3929 (2004); Yeo et al., Angew Chem Int Ed Engl 44: 5480-5483 (2005); Marin et al., Angew Chem Int Ed Engl 46: 8796-8798 (2007); Patrie et al., Anal Chem 79: 5878-5887 (2007); Ban et al., Angew Chem Int Ed Eng 47: 3396-3399 (2008); Gurard-Levin et al., Annu Rev Anal Chem (Palo Alto Calif.) 1: 767-800 (2008); Gurard-Levin et al., Biochemistry 47: 6242-6250 (2008); Mrksich, ACS Nano 2: 7-18 (2008); Tsubery et al., Langmuir 24: 5433-5438 (2008); Gurard-Levin et al., Chembiochem 10: 2159-2161 (2009); Liao et al., Chemistry 15, 12303-12309 (2009); Gurard-Levin et al., ACS Chem Biol 5: 863-873 (2010); Kim et al., Nucleic Acids Res 38: e2 (2010); Cai et al., Carbohydr Res 346: 1576-1580 (2011); Gurard-Levin et al., ACS Comb Sci 13: 347-350 (2011); Liao et al., Angew Chem Int Ed Engl 50: 706-708 (2011); Prats-Alfonso et al., Small 8: 2106-2115 (2012); Li et al., Langmuir 29: 294-298 (2013)).

In general, the disclosure provides methods of assaying activity of an intracellular enzyme, comprising (a) contacting a cell and a surface, the surface comprising an immobilized cell adhesion ligand and an immobilized substrate for the enzyme, the contacting resulting in immobilization of the cell via interaction between the cell and the immobilized cell adhesion ligand; (b) contacting the cell with a lysing solution to form a cell lysate and release the enzyme, thereby allowing contact between the enzyme and the immobilized substrate to transform the immobilized substrate to a product, the product having a different mass than the substrate; and (c) measuring the amount of the product formed using matrix-assisted laser desorption/ionization mass spectrometry (MALDI-MS) to assay the activity of the enzyme.

The methods described herein offer several advantages over existing technologies. First, the assay provides a way to acquire enzyme activity measurements from thousands of independently generated cell lysates. Existing screening assays frequently use gene expression or phenotypic changes as a readout. Next, the assay uses self-assembled monolayers for culturing cells and for reporting on enzyme activities from lysates generated by the cultured cells. This unique combination enables quantitative readouts of enzyme activities in a high throughput format. Further, the assay is label-free, whereas most screening assays require a labeled reporter. Also, the assay is easily adapted to new targets. As disclosed herein, this is achieved by simply immobilizing a substrate for the enzyme of interest onto the monolayer. Also as disclosed herein the assay requires only a small number of cells for various enzyme activities. Finally, the assay can measure activities from enzymes, such as phosphatases, which are impractical to measure in high-throughput from cell lysates using other assay technologies.

Cell-based screening is an increasingly popular tool used in drug discovery. This technology opens up the potential of conducting cell-based screens that use enzyme activity measurements as the readout. This is of significant value because cell-based screens provide more physiologically relevant information about the activity of compounds, potentially leading to better lead compounds in drug discovery efforts.

TCAL-SAMDI as disclosed herein provides a general method for conducting cell-based, chemical screening with quantitative readouts of enzymatic activity, easily adaptable to a wide range of targets.

Lysing Solution.

As discussed herein, methods of the disclosure involve contacting a cell with a lysing solution (i.e., lysis buffer). Solutions that will lyse cells (e.g., any prokaryotic, eukaryotic, or plant cell) are well known in the art. Lysis buffers contemplated herein comprise, in various embodiments, a detergent to effect lysis of the cell of interest. Detergents are a class of molecules whose unique properties enable manipulation (e.g., disruption or formation) of hydrophobic-hydrophilic interactions among molecules in biological samples. It is contemplated herein that detergents are used to lyse cells through solubilization of membrane proteins and lipids to release the cell contents.

Detergents are amphipathic molecules, meaning they contain both a nonpolar "tail" having aliphatic or aromatic character and a polar "head." Ionic character of the polar head group forms the basis for broad classification of detergents; they may be ionic (charged, either anionic (e.g., sodium dodecyl sulfate (SDS) or cationic (e.g., ethyl trimethyl ammonium bromide), nonionic (uncharged; e.g., NP-40, Brij-35, Brij-58, Tween20, Tween80, octyl glucoside, octyl thioglucoside) or zwitterionic (having both positively and negatively charged groups but with a net charge of zero; e.g., CHAPS, CHAPSO). Detergents can be denaturing or non-denaturing with respect to protein structure. Denaturing detergents can be anionic such as sodium dodecyl sulfate (SDS) or cationic such as ethyl trimethyl ammonium bromide. Non-denaturing detergents can be divided into nonionic detergents such as Triton X-100, bile salts such as cholate and zwitterionic detergents such as CHAPS. Lysis buffers also comprise, in various embodiments, salts such as Tris-HCl and/or EDTA to regulate the acidity and osmolarity of the lysate.

Surface.

The surface can be any material capable of forming a monolayer, e.g., a monolayer of alkanethiols. Particularly, the substrate may be a metal, such as Au, Ag, Pd, Pt, Cu, Zn, Fe, In, Si, $Fe_2O_3$, $SiO_2$ or ITO (indium tin oxide) glass. In various embodiments, the disclosure contemplates that a surface useful in the methods described herein comprises Au, Ag, or Cu.)

Cell Adhesion Ligand.

As discussed herein, aspects of the disclosure contemplate the use of a surface comprising an immobilized cell adhesion ligand. In various embodiments, the cell adhesion ligand comprises an amino acid sequence such as, for example and without limitation, RGD or GRTY.

Immobilized Substrate.

In various aspects, the disclosure contemplates a surface, the surface comprising an immobilized cell adhesion ligand and an immobilized substrate for an enzyme. In general, the substrate for an enzyme of interest is known in the art. For example and without limitation, if the enzyme of interest is a phosphatase, then the immobilized substrate can be a peptide sequence comprising a phosphorylated amino acid.

The substrate is immobilized to the surface using any surface chemistry known in the art, such as thiol chemistry.

Intracellular Enzyme.

The disclosure generally provides methods of assaying activity of an intracellular enzyme. Any enzyme is contemplated for use according to the methods provided herein, including but not limited to a deacetylase, acetyltransferase, esterase, phosphorylase/kinase, phosphatase, protease, methylase, demethylase, or a DNA or RNA modifying enzyme.

High Throughput Formats for SAMDI.

An improvement to the SAMDI method is disclosed herein. The improved method translates SAMDI to a high throughput format based on standard 384 and 1536 microtiter plate formats. This format uses a stainless steel plate in the size of a microtiter plate and having an array of gold-coated islands modified with a monolayer presenting maleimide groups (e.g., linkers of formula I) against a background of tri(ethylene glycol) groups. Substrates are then immobilized to each of the islands; in various embodiments, in a high throughput screen each island has the same substrate whereas in an experiment to identify active substrates for an enzyme each spot would present a different substrates (or suspected substrates). Standard robotic liquid handling equipment can be used to prepare arrays of reactions and to transfer those reaction mixtures to the array plates. The treated plates are incubated (e.g., between 30-60 minutes), washed, and a solution of matrix is applied to the surface. The plate is then loaded into a MALDI-ToF instrument, and each spot is analyzed in an automated fashion in approximately 30 minutes. Resulting data is analyzed using custom written software that can compare the location and magnitude of the peaks in the SAMDI spectra to a reference mass file unique to each set of peptides to look for specific reaction profiles based on characteristic mass shifts (i.e., −42 for deacetylation, +80 for phosphorylation, +14 for methylation). The software presents the data in a manner that can be further analyzed with standard commercial packages (such as Excel) to identify hits in a high throughput screen, or to generate heatmaps of activities. Recent work has demonstrated the screening of 100,000 molecules against the KDAC8 deacetylase (Gurard-Levin et al., ACS Comb Sci 13: 347-350 (2011)).

Modulators/Activators.

As described herein, various aspects of the disclosure provide a method of assaying activity of an intracellular enzyme, comprising (a) contacting a cell and a surface, the surface comprising an immobilized cell adhesion ligand and an immobilized substrate for the enzyme, the contacting resulting in immobilization of the cell via interaction between the cell and the immobilized cell adhesion ligand; (b) contacting the cell with a lysing solution to form a cell lysate and release the enzyme, thereby allowing contact between the enzyme and the immobilized substrate to transform the immobilized substrate to a product, the product having a different mass than the substrate; and (c) measuring the amount of the product formed using matrix-assisted laser desorption/ionization mass spectrometry (MALDI-MS) to assay the activity of the enzyme. In some embodiments, the assay is performed in the presence of one or more potential modulators of the enzyme-substrate binding; subjecting the substrate and product to mass spectrometry to produce a mass spectrum having a product signal and a substrate signal; and binding of the enzyme and the immobilized substrate is detected by correlating a signal intensity of the product to a signal intensity of the substrate to determine the extent of product formation and thereby detecting the binding of the enzyme and the immobilized substrate in the presence of the one or more potential modulators.

In some embodiments, the modulator is an inhibitor of the enzyme and immobilized substrate binding. In further embodiments, the modulator is an activator of the enzyme and immobilized substrate binding.

Multiplexing.

As described and exemplified herein, the methods of the disclosure are amenable to the multiplex format. Thus, in any of the aspects or embodiments of the disclosure, simultaneous analysis of more than one immobilized substrate is contemplated. In further embodiments, the more than one immobilized substrate is analyzed directly from a cell lysate following lysis of one or more cells on a surface.

EXAMPLES

The following non-limiting examples demonstrate a strategy for analyzing lysates from small numbers of cells, which relies on culturing cells on a monolayer that presents a peptide for cell adhesion together with a peptide substrate to report on a desired enzyme activity. In this way, cells can be cultured on the monolayer and lysed in place, where enzymes in the lysate can directly and immediately act on the immobilized substrates. The monolayer is then rinsed and analyzed by SAMDI mass spectrometry to quantitate the amount of product. By way of example, this method is applied in a 384-array format for measuring both protein tyrosine phosphatase (PTP) and caspase-3 activities. The examples also show how this platform performed in a cell-based screen to identify modulators of PTP activity.

Example 1

General Materials and Methods

Reagents.

PTP Inhibitor I (PTPI-I) was purchased from Santa Cruz Biotechnology and PHPS1 was obtained from Sigma Aldrich. Hexadecyl phosphonic acid and 2,4,6-trihodoxy-acetophenone were also purchased from Sigma Aldrich. The 10,240-chemical library was purchased from Chembridge. Amino acids and peptide synthesis reagents were obtained from Anaspec. The phosphatase substrate (pY peptide; sequence: AIpYENPFARKC (SEQ ID NO: 1)), caspase-3 substrate (CGKRKGDEVDSG (SEQ ID NO: 2)), and cyclic RGD peptides were synthesized following standard solid phase peptide synthesis protocols as previously described [Kilian et al., Angew Chem Int Ed Engl. 51(20): 4891-5 (2012)]. The Presto Blue kit, calcein-AM and ethidium homodimer-1 were purchased from Life Technologies and the cell viability assays were performed following manufacturer's instructions.

Preparation of Self-Assembled Monolayers.

Custom fabricated stainless steel plates (8×12.3 cm) were first cleaned using hexanes, ethanol and DI water. An electron beam evaporator was used to first deposit 5 nm Ti (0.02 nm/s) onto the steel plates. The evaporator was vented to oxidize the Ti layer. Next, an aluminum mask having holes in a 384-well format was placed on top of the plate and an additional 5 nm Ti (0.02 nm/s) were deposited followed by 35 nm Au (0.05 nm/s). The Au-coated steel plates were soaked overnight at 4° C. in an ethanolic solution containing a 1:4 ratio of an asymmetric disulfide terminated with a maleimide group and a tri(ethylene glycol) group and a symmetric disulfide terminated with tri(ethylene glycol) groups, with a 0.5 mM total disulfide concentration. The plates were rinsed with ethanol and then immersed in a 10 mM ethanolic solution of hexadecyl phosphonic acid for 10 minutes. After rising with ethanol and drying under air, an automated reagent dispenser (Multidrop Combi, Thermo Scientific) was used to spot 3 µL of a peptide solution consisting of 32 µM pY peptide and 8 µM cyclic RGD in 1×PBS at pH 7.5 onto the arrayed plates. The peptide immobilization solution used for duplexed phosphatase and caspase-3 activity measurements consisted of 8 µM pY peptide, 8 µM cyclic RGD and 24 µM caspase-3 peptides. All peptide immobilization steps were carried out for one hour at 37° C. in a humidity chamber.

TCAL-SAMDI Assay for PTP and Caspase-3 Activity.

HeLa cells and MDA-MB-231 cells were obtained from ATCC and cultured in αMEM (for HeLa cells) or high-glucose DMEM (for MDA-MB-231 cells) medium supplemented with 10% fetal bovine serum, glutamax, penicillin and streptomycin. All cells were cultured in a humidified incubator at 37° C. and $CO_2$. Cells were trypsinized and suspended in media, and the average number of cells per µL was counted using a hemocytometer and Countess automated cell counter (Life Technologies), and cell concentrations were adjusted to seed the desired number of cells per spot in 3 µL media. Cells were cultured on the monolayers presenting RGD and peptide substrates on steel plates or glass slides for two hours under standard growth conditions. For PTP activity assays, cells were cultured for two hours before addition of inhibitors, if any. For caspase-3 activity assays, 1 µL of 4 µM staurosporine (STS) was added to each spot (for a final concentration of 1 µM STS), and incubated for four hours. After culture, media was removed and lysis buffer (1 or 1.5 µL) was delivered manually or with an automated reagent dispenser to each spot and the lysate was allowed to react with the monolayer for one hour at 37° C. in a humidity chamber. Lysis buffer was composed of 20 mM Tris, 136 mM NaCl, 1 mM EDTA, 0.5% Triton-X 100, pH 7.4. A protease inhibitor tablet obtained from Roche was added to the lysis buffer. For caspase activity assays, 10 mM dithiothreitol was added to the lysis buffer. The surfaces were then rinsed with DI water and ethanol, and dried with air. A 30 mg/mL solution of 2,4,6-trihydroxyacetophenone in acetone was delivered to each spot on the array and the surfaces were analyzed using an AB Sciex 5800 MALDI TOF/TOF instrument in positive reflector mode. The area under the curves for the $[M+H]^+$ peaks of disulfides was measured with the Data Explorer software (AB Sciex). All experiments were repeated at least three times, with at least three spots per condition each time. Presented data represent the means and standard errors of all spots. For lysate experiments (see below for more detail), data represents the averages and standard errors from at least three independently prepared lysates. Statistical comparisons between mean activities were made using Student's t-tests.

TCAL-SAMDI Assay for Chemical Screen.

A 10,240 chemical library was used to screen for phosphatase inhibitors. For the chemical screen, 100 or 150 MDA-MB-231 cells were seeded on each spot presenting cyclic RGD and pY peptide (phosphatase substrate) and cultured for two hours. A stock solution of each compound was first prepared in DMSO then diluted in media. Each compound was delivered (1 µL) to each spot on the array to a final concentration equivalent to 10 µM and 1% DMSO. The cells were exposed to the compounds for two hours under standard cell growth conditions. After media removal, the lysis buffer with protease inhibitor was applied to each spot independently and incubated for one hour at 37° C. in a humidity chamber. The plates were then rinsed with water, ethanol, and dried under air. Matrix was applied prior to mass spectrometry analysis. As described above, the data was analyzed to quantify the levels of phosphatase activity and hits were ranked. The five compounds that produced the greatest inhibition of PTP activity on each plate were chosen for a secondary screen to confirm hits. The secondary screen was carried out following the same conditions stated above, except that each compound was tested on six spots instead of one. Additionally, some compounds tested in the secondary screen step were tested at 50 µM.

Evaluation of Dose-Dependent Inhibition by TCL-SAMDI.

MDA-MB-231 cells were seeded at 75 cells per spot on monolayers presenting phosphatase peptide substrates and cyclic RGD as described above. Following cell attachment and culture for two hours, inhibitors (1 µL solution in media) were delivered to each spot to achieve a range of final concentrations from 0 to 640 µM in media and incubated for two hours. Following media removal, the lysis buffer with protease inhibitor was applied to each spot independently and incubated for one hour at 37° C. in a humidified chamber. Plates were then rinsed with water, ethanol and dried. Matrix was applied prior to analysis by mass spectrometry. All experiments were carried out at least twice, with six spots per condition each time. Presented data represent the averages and standard errors of all spots. $IC_{50}$ values and curves were determined using GraphPad prism software.

Evaluation of Dose-Dependent Inhibition in Cell Lysates Using SAMDI.

MDA-MB-231 cells were lysed using the lysis buffer containing protease inhibitor described above to achieve the equivalent of 75 cells per 1.5 µL, after mixing with inhibitor solutions. Inhibitor solutions in lysis buffer at concentrations ranging from 0 to 640 µM were added to the lysate and 1.5 µL of the mixture was spotted on monolayers presenting cyclic RGD and phosphatase substrate. The reaction was carried out for 1 hour at 37° C. in a humidified chamber. To evaluate dose-response inhibition under standard culture conditions, MDA-MB-231 cells were plated on a 96-well plate at a density of 6,400 cells per well and cultured for two hours. Culture medium containing inhibitors at final concentrations ranging from 0 to 300 µM and 1% DMSO were delivered to each well and culture proceeded for another two hours. The mixture containing media and inhibitor was removed from each well and centrifuged. Lysis buffer containing protease inhibitor was applied to each well in the plate and incubated for 10 minutes at room temperature. The lysate was collected and added to the corresponding cell pellet for each inhibitor concentration sample. The lysate (1.5 µL) was spotted on monolayers presenting RGD and phosphatase substrate. Protein concentrations were measured using a BCA assay (Santa Cruz Biotechnology), following manufacturer instructions. Sample analysis using SAMDI followed as described above. Presented data represents the averages and standard errors from at least three independently prepared lysates. $IC_{50}$ values and curves were determined using GraphPad prism software.

Cell Viability Assays.

The Presto Blue assay was performed using MDA-MB-231 cells seeded at 6,400 cells per well in a 96 well plate format. After a two hour culture period, medium containing inhibitors at a range of concentrations from 0 to 300 µM was added to each well and incubated for two hours. PrestoBlue reagent was added to the wells, incubated for 25 minutes, and fluorescence was measured using a Cytation 3 (BioTek) plate reader. For calcein-AM and ethidium homodimer-1 staining, MDA-MB-231 cells were seeded on glass slides presenting monolayers of RGD and phosphatase peptide substrate at 75 cells per spot. After two hours of culture, 1 µL of media containing inhibitors for a final concentration of 10 µM and 80 µM was added to each spot and incubated for an additional two hours. Media was removed and a solution of calcein-AM and ethidium homodimer-1 in PBS were delivered (3 µL) to each spot and incubated at 37° C. for 20 minutes. Each spot was imaged using an epifluorescent microscope and cells were counted using ImageJ Cell Counter plug-in.

Z' Factor Determination.

A gold-coated steel plate with monolayers arrayed in a 384-well format was used to seed 150 MDA-MB-231 cells per spot. After two hours of culture, DMSO was added to a final concentration of 1% on 160 spots (negative controls) and PTPI-I was added to a final concentration of 300 µM, 1% DMSO, on 160 spots (positive controls). After two hours, the media was removed and lysis buffer applied for 1 hour at 37° C. Sample analysis using SAMDI followed as described above. Z' factor was calculated using the following equation:

$$Z'\text{-factor} = 1 - \frac{(3\sigma_{c+} + 3\sigma_{c-})}{|\mu_{c+} - \mu_{c-}|}$$

where $\sigma_{c+}$ and $\sigma_{c-}$ represent the standard deviations of the positive and negative controls, respectively, and $\mu_{c+}$ and $\mu_{c-}$ represent the means of the positive and negative controls, respectively.

Example 2

TCAL-SAMDI Assay of Phosphatase Activity

Figure 2:
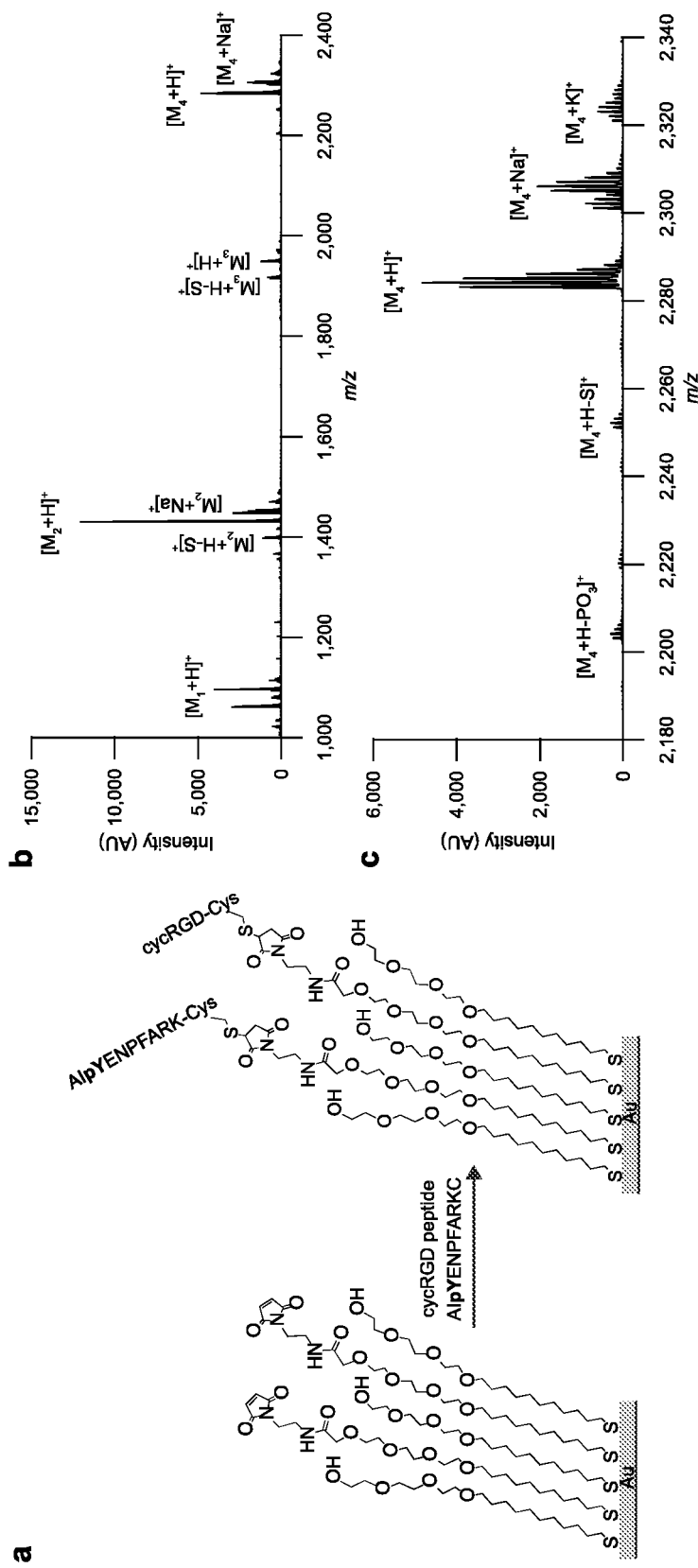
FIG. 2 shows SAMDI on monolayers with two peptides. (a) Two peptides with terminal cysteines (a cell adhesion ligand (cyclic RGD peptide—cycRGD) and an phosphatase substrate (AlpYENPFARKC (SEQ ID NO: 1)) are immobilized on alkanethiolate monolayers with 10% of the molecules presenting maleimides and 90% terminated with tri(ethylene glycol). (b) SAMDI spectrum of a monolayer with immobilized RGD peptide and phosphatase peptide. M1: alkanethiolate with RGD, M2: alkyldisulfide with RGD, M3: alkanethiolate with phosphatase peptide, M4: alkyldisulfide with phosphatase peptide (c) The same spectrum, showing the portion of the spectrum used for PTP activity analysis.

First, an array of monolayers was prepared to measure PTP activity in HeLa cell cultures. Each monolayer was composed of alkanethiolates terminated with maleimide groups at a density of 10% relative to total alkanethiolates, against a background of tri(ethylene glycol) groups (FIG. 2a). A solution containing a cyclic peptide having the cell adhesion RGD motif was applied together with a peptide having a phosphorylated tyrosine residue (AIpYENP-FARKC (SEQ ID NO: 1)) [Li et al., Langmuir 29: 294-298 (2013)] to report on phosphatase activity, and the peptides were immobilized onto the monolayer. The RGD motif is found in fibronectin [Ruoslahti, Annu Rev Cell Dev Biol 12: 697-715 (1996)] and mediates cell adhesion and spreading by binding to integrin receptors [Houseman et al., Biomaterials 22: 943-955 (2001); Roberts et al., Journal of the American Chemical Society 120: 6548-6555 (1998)]. The monolayers were formed on a stainless steel plate having an array of gold spots (2.8-mm diameter) positioned to match a 384-well plate format, as recently described [Gurard-Levin et al., ACS Comb Sci 13: 347-350 (2011); Patel et al., J Biomol Screen, 20(7): 842-8 (2015)]. The area surrounding each spot consisted of a thin layer of evaporated titanium with a monolayer of hexadecylphosphonic acid formed on the titanium dioxide to render the outer area hydrophobic, enabling droplets to be isolated on the monolayer-coated gold spots. HeLa or MDA-MB-231 cells were plated and cultured on the monolayers in individual volumes of media (3 µL) that were isolated on each spot (FIG. 3a). After two hours in culture, the media was rapidly removed from all spots with a robotic liquid-handling instrument and immediately replaced with lysis buffer (1 µL). After incubating the plates with lysis buffer for one hour, the plates were rinsed with water and then ethanol and analyzed by mass spectrometry.

Figure 3:
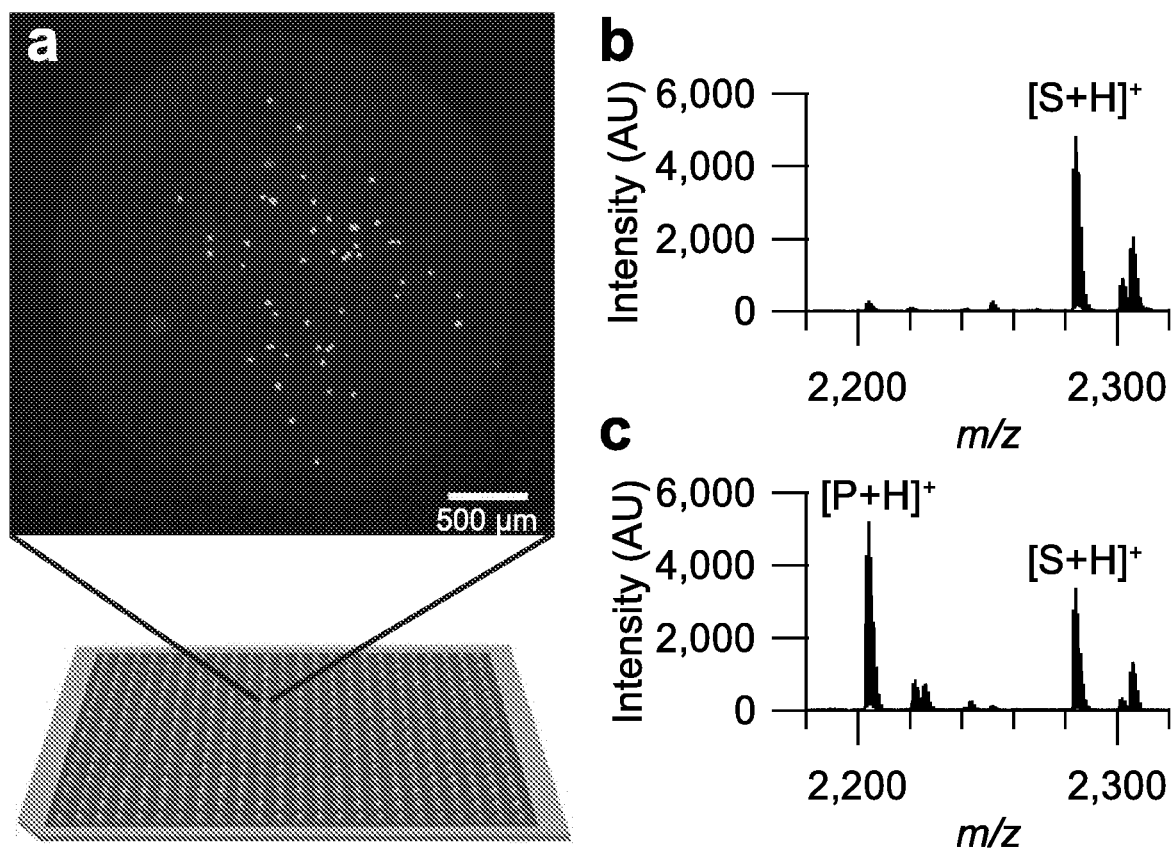
FIG. 3 depicts Tandem Culture and Lysis SAMDI (TCAL-SAMDI). (a) Cells (MDA-MB-231) are cultured on monolayers presenting both cell adhesion ligands and a phosphatase substrate, on a 384-spot plate. Green: live cells, Red: dead cells and gold spot. (b) A SAMDI spectrum from a spot without cells. (c) A SAMDI spectrum after lysis of 50 cells.

Prior to analysis, the plates were treated with 2,4,6-trihydroxyacetophenone (THAP) matrix and MALDI spectra were collected for each monolayer island. Performing MALDI on spots without cells produced spectra with peaks at mass-to-charge (m/z) values corresponding to the peptide-alkanethiolate conjugates as well as disulfides formed between a peptide-modified alkanethiolate and a background tri-ethylene glycol-presenting alkanethiolate, along with Na$^+$ adduct peaks (FIG. 2b, 2c). After lysis of cells on the spots, dephosphorylation of the peptide substrate resulted in the formation of a product peak with a mass shift of −80 Da (FIG. 3). It was confirmed that the peak at −80 Da relative to the substrate peak is the product peak by performing the same assay with a substrate of a different mass, in which case no peak appeared at the mass corresponding to the original product peak, but rather, at −80 Da relative to the new substrate.

Figure 4:
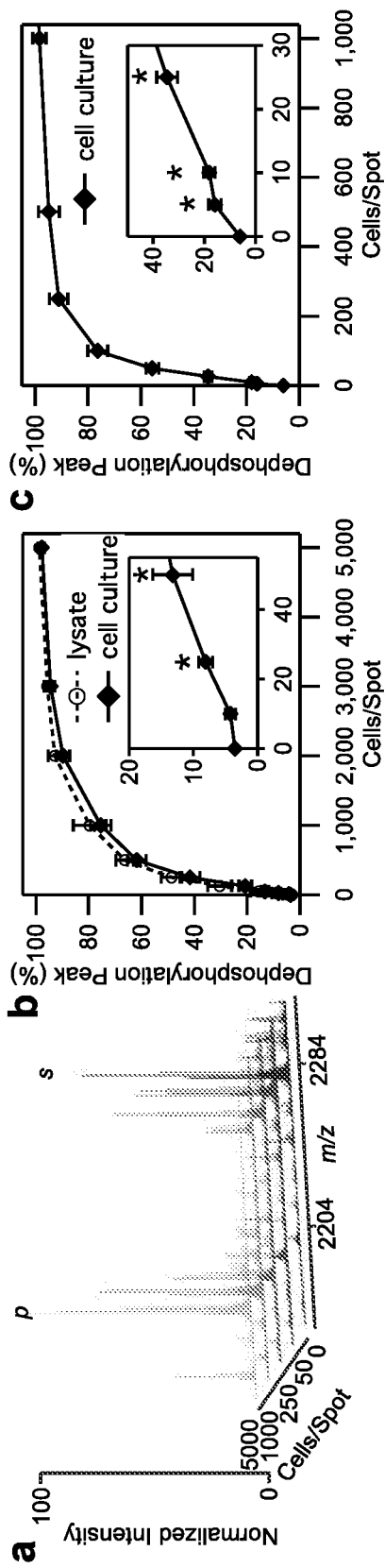
FIG. 4 shows an enzyme activity measurement with TCAL-SAMDI. (a) SAMDI-MS spectra showing the conversion of substrate (s) to product (p) as the number of HeLa cells cultured and lysed on monolayer-coated gold spots increases. Quantification of the dephosphorylation peak fraction, defined as the area under the curve of the product peak relative to that of the substrate and product peaks in the SAMDI spectra, resulting from culturing and lysing (b) HeLa cells and (c) MDA-MB-231 cells on monolayers presenting adhesion and substrate peptides. Insets in (b) and (c) are magnified regions of the graphs. (*: $P<0.01$).
Figure 5:
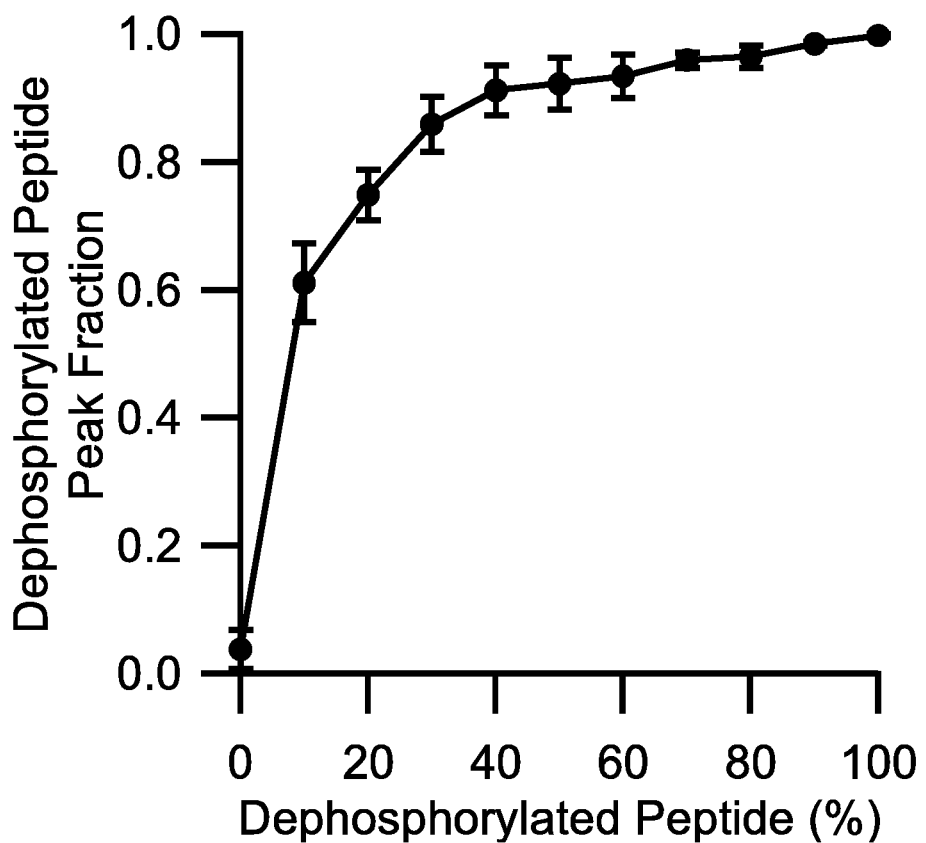
FIG. 5 shows a calibration curve relating the dephosphorylated peptide peak fraction measured by SAMDI to the ratio of the dephosphorylated peptide to the phosphorylated peptide used during immobilization onto the monolayer.

It was observed that as the number of cells cultured on a spot increased, the relative intensity of the product peak grew larger while that for the substrate peak diminished (FIG. 4a). The dephosphorylation peak fraction was determined by measuring the area under the curve for the product peak and dividing by the sum of areas for the substrate and product peaks. Because of differences in ionization efficiencies between the phosphorylated and dephosphorylated molecules, to calculate product yield, it would be necessary to scale the observed dephosphorylation peak fractions using a calibration curve as shown in FIG. 5. It was observed that the dephosphorylation peak fraction increased with HeLa cell number, before plateauing near 2,000 cells per spot. (FIG. 4b). With this method, phosphatase activity was measured from as few as 25 cells per spot (FIG. 4b). With MDA-MB-231 cell cultures, we measured PTP activity from only 5 cells per spot (FIG. 4c).

To determine if culturing cells on the monolayer would interfere with enzyme activity on immobilized substrates, phosphatase activity from previously prepared HeLa cell lysates was also measured. Here, HeLa cells were not cultured on the monolayers but rather lysed and then applied to the monolayers to measure PTP activity (FIG. 4b, dashed line). Comparing these two methods revealed that the activity measured with TCAL-SAMDI (FIG. 4b, black line) was not significantly different at most cell concentrations from the activity measured from cell lysates (FIG. 4b, dashed line). This result demonstrated that culturing and lysing cells directly on the surface did not interfere with the ability of enzymes to act on the immobilized substrate or the ability to perform SAMDI on these surfaces.

Example 3

Duplexing Enzyme Activity Measurements with TCAL-SAMDI

Figure 6:
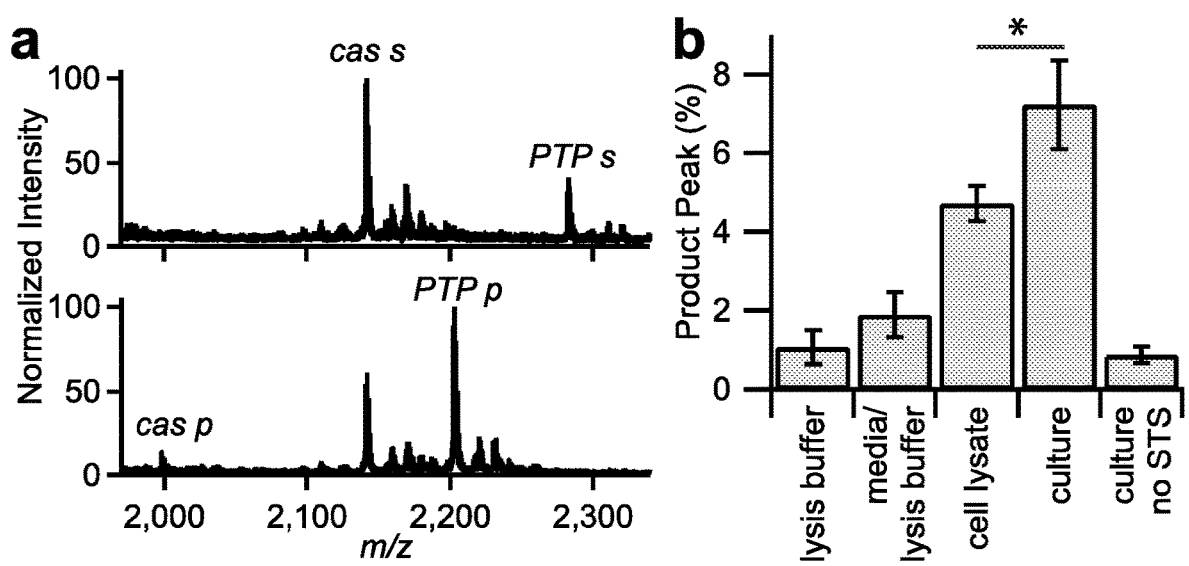
FIG. 6 shows duplexing enzyme activity measurements with TCAL-SAMDI. (a) SAMDI spectra of a spot with no cells (top) and with 10,000 cells (bottom) shows the conversion of two substrates (PTP s: PTP substrate; cas s: caspase-3 substrate) to their products when cells are cultured, treated with STS, and lysed on the surface. (b) Caspase-3 activity measured by SAMDI (*: $P<0.05$).

One significant benefit of mass spectrometric assays is that they are well suited to multiplexed formats [Min et al., Angew Chem Int Ed Engl 43: 5973-5977 (2004)]. To illustrate this advantage, monolayers were prepared that had the adhesion peptide, the phosphatase substrate and a peptide substrate for the protease caspase-3 (CGKRKGDEVDSG (SEQ ID NO: 3) [Su et al., Anal Chem 78, 4945-4951 (2006)]. HeLa cells were cultured on monolayers presenting these three peptides for one hour and then apoptosis was induced by adding staurosporine to the medium [Bernard et al., Cell Death Differ 8: 234-244 (2001)]. After four hours of treatment with staurosporine, the cells were lysed as described above and the monolayers were similarly analyzed by SAMDI mass spectrometry. The mass spectra clearly show the conversion of both substrates to their corresponding products (FIG. 6a), demonstrating the ability to duplex activity measurements with TCAL-SAMDI. In addition to peak for the dephosphorylated peptide, we also observed a peak corresponding to the caspase-3 product at 144 Da lower than the initial substrate mass (FIG. 6a). Monolayers treated with lysis buffer and media, as well as monolayers with cells but without staurospaurine show a lack of the caspase-3 product (FIG. 6b). Interestingly, the conversion of substrate to product was significantly greater when cells were lysed directly on the surface, compared to the conversion observed from applying the cell lysate to the monolayer. This benefit of the TCAL assay may reflect a loss of activity of the enzyme activity that accumulates in time.

Example 4

Assaying Small Molecule Modulators in Cell Culture

Figure 7:
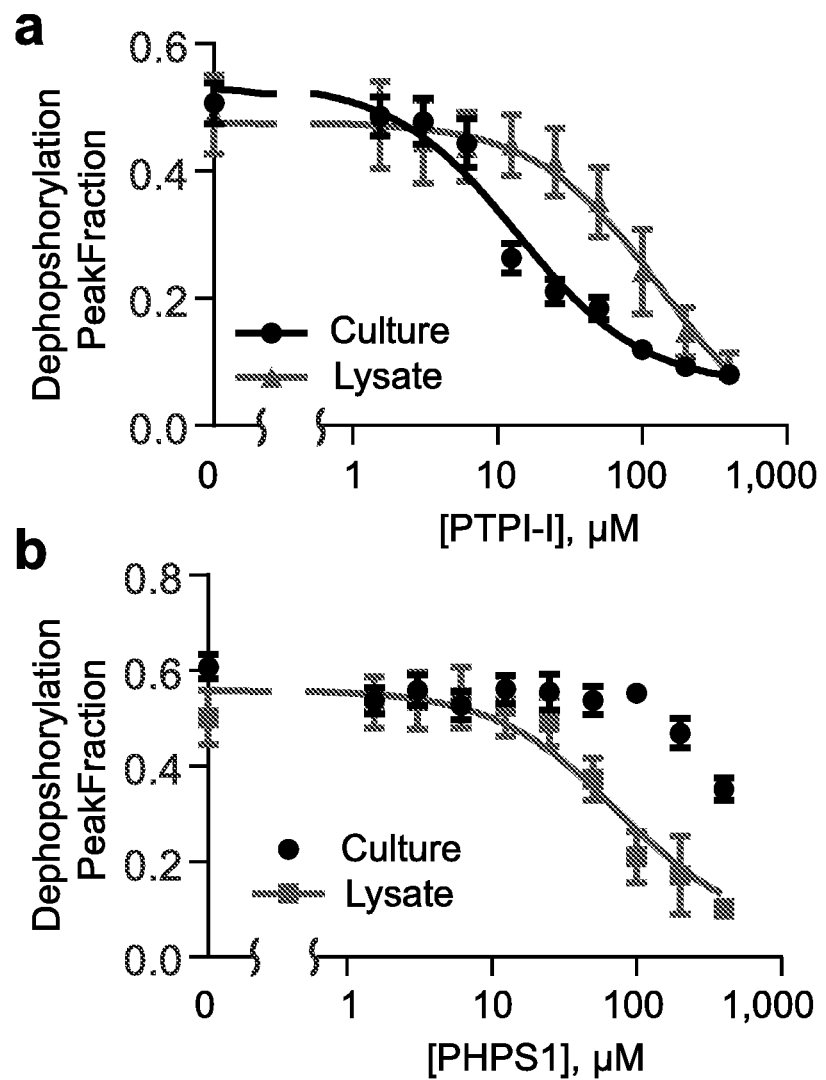
FIG. 7 depicts inhibitor characterization with TCAL-SAMDI. (a) SAMDI analysis of PTP activity in the presence of the inhibitors PTPI-I and (b) PHPS1.

The TCAL-SAMDI assay was next used to evaluate the effect of two reported PTP inhibitors—the covalent inhibitor PTP Inhibitor I (PTPI-I) [Arabaci et al., Journal of the American Chemical Society 121: 5085-5086 (1999)] and the competitive inhibitor PHPS1 [Hellmuth et al., Proc Natl Acad Sci USA 105: 7275-7280 (2008)]—on cultured cells. Treatment of cells with the PTPI-I produced inhibition of PTP activity with an $IC_{50}$ of 14 µM (FIG. 7a). Treatment of cell lysate (rather than cells) with PTPI-I, followed by application of the lysate to the monolayer, also resulted in PTP inhibition with an $IC_{50}$ of 83 µM. In contrast, treatment of cells with the competitive inhibitor, PHPS1, did not show PTP inhibition even for an inhibitor concentration of 160 µM (FIG. 7b). However, treatment of cell lysate with PHPS1 inhibited PTP activity with an $IC_{50}$ of 75 µM. This result reveals that the TCAL assay is not suited for detection of reversible inhibitors of the enzyme whose activity is being measured because removal of the culture medium (which includes the extracellular inhibitor) and replacement with lysis buffer will lower the concentration of the inhibitor by dilution and shift the equilibrium toward the unbound state.

Example 5

Screening with TCAL-SAMDI

A screen was performed where 10,240 small molecules in MBD-231 cells were evaluated to identify those that modulate phosphatase activity. It was found that cultures having 100-150 cells/spot resulted in approximately equal-sized peaks for the substrate and product peptides in the SAMDI spectra. This small number of cells required in the assay means that the entire screen could be performed with just one million cells. The Z'-factor, a commonly used statistical measure of assay performance, was also measured, and a Z'-factor of 0.66 was found [Zhang et al., J Biomol Screen 4, 67-73, (1999)].

A primary screen was carried out by applying one compound per spot, using approximately 30 plates for the entire screen. After culturing cells on the chips for 2 hours, solutions of each compound (1 µL) were added to the media (3 µL) on each spot on the array so that the resulting compound concentration was 10 µM with 1% DMSO. The cells were incubated for 2 hours, media was removed, lysis buffer was incubated on each spot for 1 hour, and the plates were analyzed by SAMDI. The five compounds that produced the greatest inhibition of PTP activity on each plate were analyzed in a secondary screening step to verify the activity. This process identified four compounds of interest that were investigated further.

Figure 8:
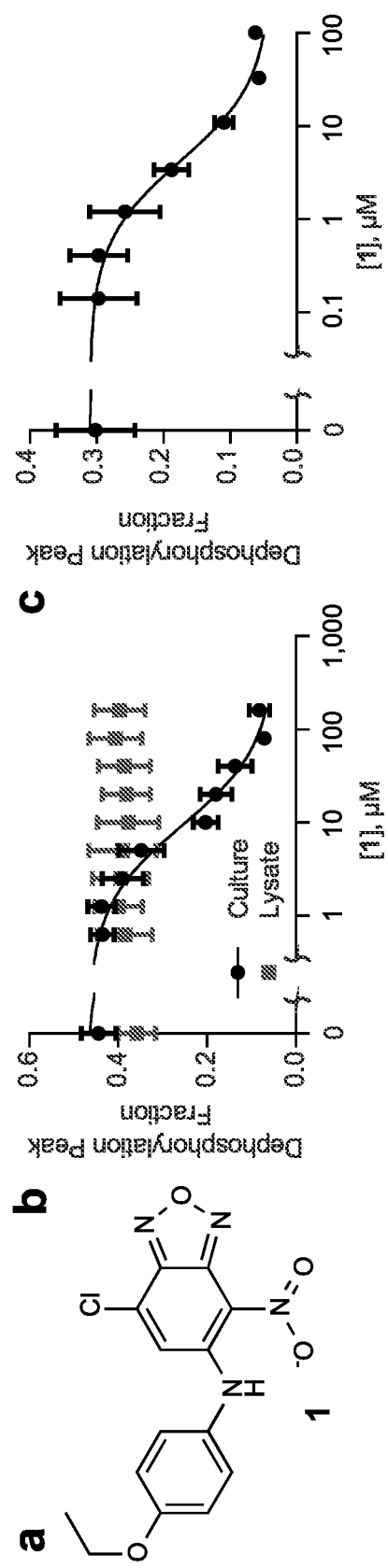
FIG. 8 depicts Compound 1 identified by chemical screening via TCAL-SAMDI. (a) Chemical structure of 1. (b) SAMDI analysis of PTP activity measured from MDA-MB-231 cells cultured on the monolayer and from lysate applied to the monolayer, both treated with 1. (c) SAMDI analysis of lysate from cells cultured in 96-well plates and treated with 1.
Figure 9:
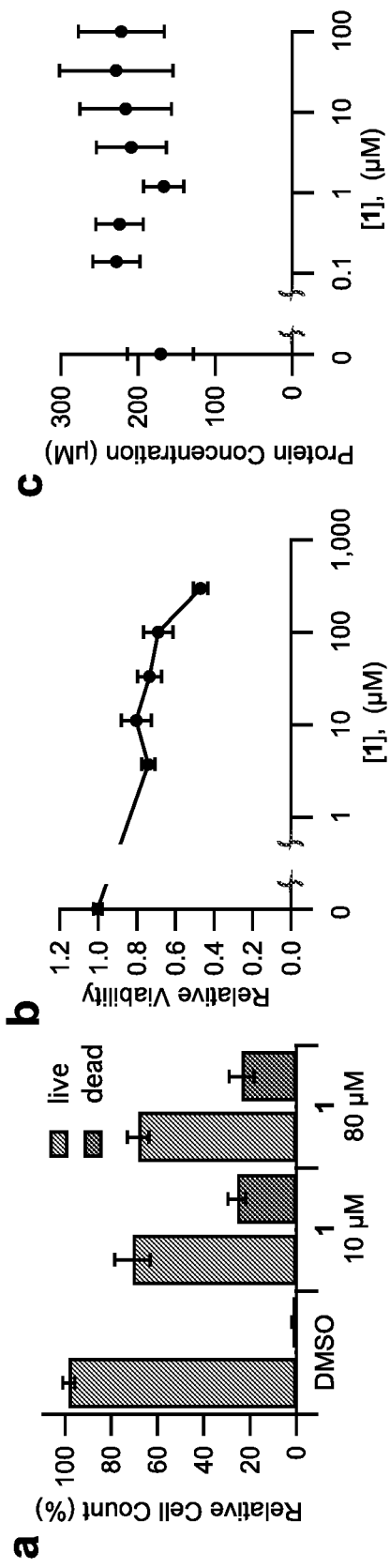
FIG. 9 shows control experiments of compound 1. (a) The cell counts of live cells (cells stained with calcein-AM) and dead cells (cells stained with ethidium homodimer) relative to the total cell count observed in cells treated with DMSO only. (b) Viability, measured by the PrestoBlue assay, of cells treated with 1, relative to cells treated with DMSO only. (c) Protein concentrations of lysates prepared from cells cultured in 96-well tissue culture plates and treated with 1 for 2 hours, measured by the BCA assay.

Compound 1 (FIG. 8a) reduced PTP activity nearly completely with an $IC_{50}$ of 9 µM (FIG. 8b). However, it was found that the compound did not directly inhibit the phosphatase because it was inactive when tested on cell lysates (FIG. 8b). It was also verified that the reduced activity was not an artifact stemming from the detachment of cells by counting the number of cells per spot (FIG. 9a). Addition of compound 1 did decrease cell viability (approximately 30% at 100 µM of 1), but this decrease was small compared to the observed inhibition of PTP activity (FIG. 9a, 9b). As an additional control to ensure that the reduction in PTP activity was not an artifact resulting from a loss of protein, lysates were prepared from cells treated with the compound while being cultured in standard 96-well tissue culture plates. Treatment of monolayers with these lysates confirmed that 1 reduced PTP activity, with a similar $IC_{50}$ of 4.2 µM (FIG. 8c), and this was not due to a decrease in protein concentration in the lysates (FIG. 9c).

Discussion

The foregoing examples demonstrate an efficient method for isolating lysates from cultured cells and assaying those lysates for enzyme activities. The efficiency of this process—which avoids the need to physically collect and manipulate the lysate—makes the method well-suited to high throughput applications comprising tens of thousands of distinct assay compositions. The disclosure illustrates the method with assays of phosphatase activity and a cell-based screen to identify molecules that regulate phosphatase activities by acting on upstream targets.

The method is enabled by two properties of the self-assembled monolayers. First, the monolayers give excellent control over the ligand-receptor interactions at the interface, allowing the surface to simultaneously mediate cell adhesion and to present a peptide that serves as a substrate to probe the desired enzyme activity. Were the surface not inert to non-specific protein adsorption—which is a common challenge with many substrates used in bioanalytical methods—the peptide substrate would be blocked from interacting with the enzymes by way of an adsorbed protein layer. Second, monolayers of alkanethiolates on gold are compatible for analysis by MALDI mass spectrometry and therefore the assays can be performed in a label-free format. This is particularly significant because it allows measurement of virtually any enzyme activity. No other surface chemistry—including common hydrogel polymer layers or alkylsiloxane monolayers—has been shown to combine these two benefits and therefore the TCAL-SAMDI method offers a new capability in bioassays.

The measurement of phosphatase activities in the present disclosure is also significant because these activities are extremely challenging to measure in cell lysates. The commonly used colorimetric assay based on p-nitrophenylphosphate (pNPP), which undergoes a shift in absorbance after dephosphorylation, is not able to discriminate between the activities of many phosphatases (acid, alkaline, protein tyrosine and serine/threonine). Assays that report on the generation of free phosphate ion that is released from a phosphopeptide of choice, such as the commonly used malachite green assay, can offer greater specificity, but are incompatible with lysate samples because of the difficulty involved in eliminating sources of phosphate present in the cell. The SAMDI assay can be used with any peptide substrate and therefore provide a more specific response on activity. Thus, there are no currently available phosphatase activity assays other than the TCAL assay that can be used to conduct a cell-based screen of protein tyrosine phosphatase activity specifically. While this alone is valuable, the method can also be extended to a broad range of enzyme activities, including glycosyltransferases, deacetylases, kinases, proteases, and others [Ban et al., Nat Chem Biol 8: 769-773 (2012); Gurard-Levin et al., ACS Chem Biol 5: 863-873, (2010); Kuo et al., Anal Chem 85: 10635-10642 (2013); Min et al., Angew Chem Int Ed Engl 43: 5973-5977 (2004); Mrksich, ACS Nano 2: 7-18 (2008); Su et al., Anal Chem 78: 4945-4951 (2006)].

An important advantage of the TCAL assay is that it does not require the lysate to be physically manipulated. At the time of the assay, the media is removed from the cell cultures and a lysis buffer is applied to the cells. No further manipulation is required because the lysate that is generated is in contact with the monolayer presenting the substrate for the relevant enzyme activity. For this reason, the TCAL method disclosed herein does not introduce any time delay between generating the lysate and assaying for activities; these time delays often lead to losses of enzyme activities, as does adsorption of proteins from the sample to the walls of pipettes and wells. Because the lysate is not manipulated in TCAL, it is possible to use smaller volumes of lysate.

An important application of the TCAL method is in screening libraries of small molecules that modulate biochemical activities in cultured cells. Cell-based screens have been particularly important in those cases where a desired downstream biochemical activity is modulated—but where there exist many distinct targets that are relevant—or where a phenotypic response is desired. Further, cell-based assays have the advantage that they do not identify as hits those molecules that are cytotoxic or that are unable to cross the membrane. However, it can be challenging to develop the reagents required in a cell-based assay. For example, FRET-based reporters of kinase activities [Ting et al., Proc Natl Acad Sci USA 98: 15003-15008 (2001); Zhang et al., Proc Natl Acad Sci USA 98: 14997-15002 (2001)] have required a substantial effort to develop, and those assays have a limited quantitative resolution. In other cases, it can be difficult to deliver the reagent to the appropriate cellular compartment. The methods disclosed herein are readily formatted to detect many enzyme activities. Further, the assay is performed after the cell has been lysed and therefore avoids limitations of getting a reagent into the cell.

The TCAL method provides a practical method for performing cell-based assays. Gold-coated glass substrates are already commercially available, and metal plates like those used in this work could similarly be made. All components of the monolayer are also commercially available and the required amount of chemicals needed to form the monolayer is minimal. Our 10,000 compound screen required 32 plates for the initial screen, which required approximately twenty hours to analyze by mass spectrometry. The same liquid handling robotic instruments were used for this screen as are used for typical high-throughput screens. Standard cell culture was used, though the number of cells required was very small compared to most cell-based assays. The volume of media per assay (4 µL) and amount of screening compound (0.25 nmol) was very small compared to most assays, minimizing reagent costs. A commercially available MALDI-TOF instrument was used to read the plates. Available software that analyzes the area under the peaks in the mass spectra was used to determine activity, with some post-processing in Microsoft Excel, requiring only a few hours to process the data from 32 plates. Hence, as a screening assay, the TCAL method is reasonably practical, cost-efficient and rapid.

The TCAL method enables a broad range of cell-based assays that have as an endpoint a biochemical activity. As such, this method removes the constraints stemming from the incompatibility of many enzyme activity assays with the cellular environment. By integrating the cell culture with the assay on the same spot, the TCAL method requires, in various embodiments, only tens of cells. Further, because the method uses 384-array plates, it can take advantage of available liquid handling and automation tools.

Example 6

Measurement of Enzyme Activity from Single Cells

MDA-MB-231 cells were suspended in media as disclosed herein, but at a concentration of 2 cells/µL. Next, 0.5 µL of the cell suspension was distributed onto a 1536-spot SAMDI plate with monolayers presenting cyclic RGD peptides and the phosphatase substrate. The cells were cultured for one hour, then media was removed by vacuum and 75 nL of lysis buffer (20 mM Tris, pH 7.2, 136 mM NaCl, 1 mM EDTA, 0.1% Igepal CA-630, 1 mM dithiothreitol, 5% glycerol, protease inhibitor cocktail (Roche Mini EDTA-free, 1 tablet per 10 mL)) was applied to each spot with a Thermo Scientific Multidrop Combi nL. The plate was incubated for 2.5 hours at 37° C., then rinsed with water and ethanol. Matrix was applied and the plate was read by SAMDI MS.

Figure 10:
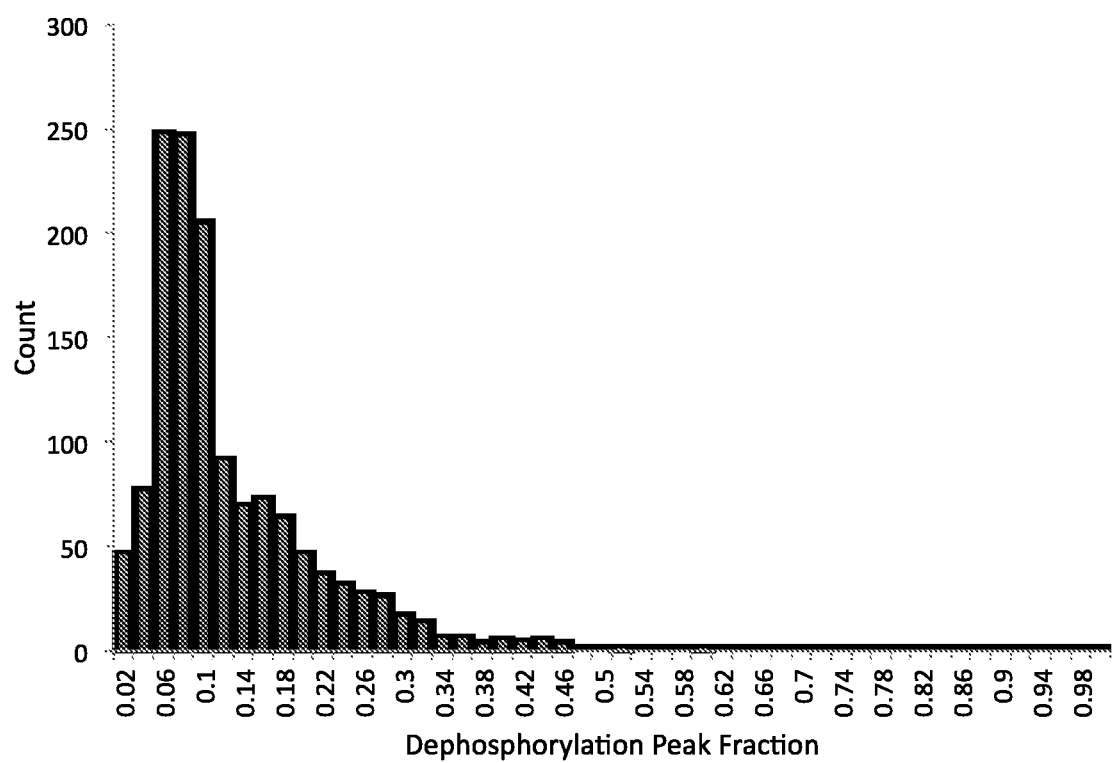
FIG. 10 depicts measurements of phosphatase activity from single cells and small numbers of cells by TCAL SAMDI.

This process enabled the acquisition of hundreds of measurements from single cells and small numbers of cells, resulting from an expected approximate Poisson distribution due to the method of dispensing cells from a cell suspension onto the 1536-spot plate. The resulting measurements of dephosphorylation are shown in FIG. 10.

What is claimed is:

1. A method of assaying activity of an intracellular enzyme, comprising:
   (a) contacting a surface with a cell suspended in media, the surface comprising a monolayer comprising an immobilized cell adhesion ligand and an immobilized substrate for the intracellular enzyme, the contacting resulting in immobilization of the cell via interaction between the cell and the immobilized cell adhesion ligand;
   (b) culturing the cell on the surface;
   (c) contacting the cultured cell with a lysing solution to form a cell lysate and release the intracellular enzyme, thereby allowing contact between the intracellular enzyme and the immobilized substrate to transform the immobilized substrate that was acted on by the intracellular enzyme to a product, the product having a different mass than the immobilized substrate; and
   (d) measuring the amount of the product formed using matrix-assisted laser desorption/ionization mass spectrometry (MALDI-MS) to assay the activity of the intracellular enzyme.

2. The method of claim 1, wherein the surface comprises a multi-well plate.

3. The method of claim 1, wherein the surface comprises gold, silver, or copper.

4. The method of claim 1, wherein at least one of the immobilized substrate and the immobilized cell adhesion ligand comprises a peptide.

5. The method of claim 4, wherein the peptide is bound to the surface via a cysteine residue.

6. The method of claim 1, wherein the immobilized cell adhesion ligand comprises a RGD peptide.

7. The method of claim 1, wherein at least one of the immobilized cell adhesion ligand and the immobilized substrate is bound to the surface via a linker.

8. The method of claim 7, wherein the linker, the surface, and the at least one of the immobilized cell adhesion ligand and the immobilized substrate has a structure of formula I:

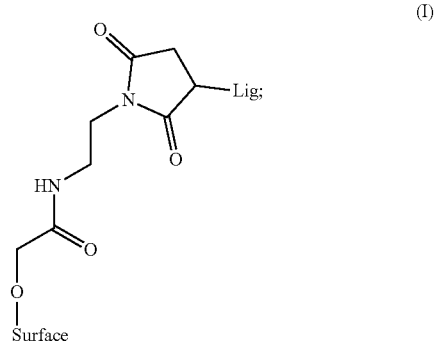

and Lig comprises the immobilized cell adhesion ligand or the immobilized substrate.

9. The method of claim 7, wherein the monolayer comprises (i) the linker and (ii) an ethylene glycol and a $C_{2-20}$ alkylene moiety.

10. The method of claim 7, wherein the monolayer is attached to the surface via a thiol bond.

11. The method of claim 1, wherein the intracellular enzyme is a deacetylase, acetyltransferase, esterase, phosphorylase/kinase, phosphatase, protease, methylase, demethylase glycosyltransferase, or a DNA or RNA modifying enzyme.

12. The method of claim 11, wherein the immobilized substrate comprises an acylated peptide and the product comprises a deacylated peptide.

13. The method of claim 11, wherein the immobilized substrate comprises a phosphorylated peptide and the product comprises a dephosphorylated peptide.

14. The method of claim 11, wherein the immobilized substrate comprises a methylated peptide and the product comprises a demethylated peptide.

15. The method of claim 1, further comprising washing the surface after immobilizing the cell on the surface and before lysing the cell to remove all cells not immobilized onto the surface.

16. The method of claim 1, wherein the surface comprises a second immobilized substrate that associates with a second enzyme in the cell lysate to form a second product, the second product having a different mass than the second substrate.

17. The method of claim 1, wherein the lysate comprises a potential modulator of binding of the intracellular enzyme and the immobilized substrate; and the activity of the intracellular enzyme assayed indicates the potential modulator's effect on the binding of the intracellular enzyme and the immobilized substrate in the presence of the potential modulator.

18. The method of claim 17, wherein the potential modulator is an inhibitor of the intracellular enzyme and immobilized substrate binding.

19. The method of claim 17, wherein the potential modulator is an activator of the intracellular enzyme and immobilized substrate binding.

20. The method of claim 1, wherein the culturing takes place for at least one hour before lysing the cell.

21. The method of claim 20, wherein the culturing takes place for about two hours before lysing the cell.

22. The method of claim 1, wherein 2, 5, 10, 20, 50, or 100 cells are applied to the surface.

* * * * *

SEQUENCE LISTING

<160> NUMBER OF SEQ ID NOS: 3

<210> SEQ ID NO 1
<211> LENGTH: 11
<212> TYPE: PRT
<213> ORGANISM: Artificial Sequence
<220> FEATURE:
<223> OTHER INFORMATION: Synthetic polypeptide

```
<220> FEATURE:
<221> NAME/KEY: MISC_FEATURE
<222> LOCATION: (3)..(3)
<223> OTHER INFORMATION: Phosporlyated Tyrosine

<400> SEQUENCE: 1

Ala Ile Tyr Glu Asn Pro Phe Ala Arg Lys Cys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 2

Cys Gly Lys Arg Lys Gly Asp Glu Val Asp Ser Gly
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 3

Cys Gly Lys Arg Lys Gly Asp Glu Val Asp Ser Gly
1               5                   10
```